(12) United States Patent
Reinhold

(10) Patent No.: US 8,718,748 B2
(45) Date of Patent: May 6, 2014

(54) SYSTEM AND METHODS FOR MONITORING AND ASSESSING MOBILITY

(75) Inventor: Ralph R. Reinhold, Elgin, IL (US)

(73) Assignee: Kaliber Imaging Inc., Elgin, IL (US)

( * ) Notice: Subject to any disclaimer, the term of this patent is extended or adjusted under 35 U.S.C. 154(b) by 0 days.

(21) Appl. No.: 13/432,516

(22) Filed: Mar. 28, 2012

(65) Prior Publication Data

US 2012/0253201 A1 Oct. 4, 2012

Related U.S. Application Data

(60) Provisional application No. 61/468,666, filed on Mar. 29, 2011.

(51) Int. Cl.
*A61B 5/11* (2006.01)

(52) U.S. Cl.
USPC ........... 600/473; 600/407; 600/424; 600/547; 600/558

(58) Field of Classification Search
USPC .......................... 600/407, 473, 424, 547, 558
See application file for complete search history.

(56) References Cited

U.S. PATENT DOCUMENTS

| | | | |
|---|---|---|---|
| 4,898,457 A * | 2/1990 | Alexeev et al. ............... | 359/786 |
| 7,244,231 B2 | 7/2007 | Dewing et al. | |
| 7,570,805 B2 | 8/2009 | Gu | |
| 7,956,862 B2 | 6/2011 | Zhang et al. | |
| 7,988,647 B2 | 8/2011 | Bunn et al. | |
| 8,050,461 B2 | 11/2011 | Shpunt et al. | |
| 8,052,623 B2 | 11/2011 | Haimerl et al. | |
| 8,077,964 B2 | 12/2011 | Berestov et al. | |
| 8,090,194 B2 | 1/2012 | Golrdon et al. | |
| 8,150,142 B2 | 4/2012 | Freedman et al. | |
| 8,553,103 B1 * | 10/2013 | Samadani et al. ......... | 348/223.1 |
| 2001/0006367 A1 * | 7/2001 | Oda ............................... | 340/567 |
| 2003/0179303 A1 * | 9/2003 | Bittner ....................... | 348/240.3 |
| 2003/0214640 A1 * | 11/2003 | Kimura et al. ................ | 353/122 |
| 2005/0065617 A1 * | 3/2005 | Moctezuma de la Barrera et al. ............................ | 623/908 |
| 2007/0115099 A1 * | 5/2007 | Hamada ..................... | 340/426.1 |
| 2007/0270214 A1 * | 11/2007 | Bentley ........................... | 463/30 |
| 2008/0150913 A1 * | 6/2008 | Bell et al. ....................... | 345/175 |
| 2010/0135550 A1 * | 6/2010 | Arnon .......................... | 382/128 |
| 2010/0228144 A1 * | 9/2010 | Labat ............................ | 600/558 |
| 2011/0001935 A1 * | 1/2011 | Reale et al. ..................... | 353/28 |
| 2012/0056982 A1 * | 3/2012 | Katz et al. ....................... | 348/43 |
| 2012/0314085 A1 * | 12/2012 | Gohshi et al. ................. | 348/164 |

OTHER PUBLICATIONS

Aptina (2008) 1/3-inch Wide-VGA CMOS Digital Image Sensor MT9V034 [Data Sheet].
GS Settles (2001) Schlieren and Shadowgraph Techniques: Visualizing Phenomena in Transparent Media, Springer, Berlin.
Cypress (2011) STAR1000 1M Pixel Radiation Hard CMOS Image Sensor, [Data Sheet] Cypress Semiconductor Corp, San Jose, CA.
Photon Focus (2004) Photometry versus Radiometry, AN008 V1.1, Photonfocus AG, Locken Switzerland.

* cited by examiner

*Primary Examiner* — Baisakhi Roy
(74) *Attorney, Agent, or Firm* — Michael Best & Friedrich LLP

(57) ABSTRACT

A system and methods are provided relating generally to physical activity and more specifically to tools for monitoring and assessing physical activity by capturing images of a subject's movement including range of motion, gait, balance and activities of daily living at different time periods and comparing those images to stored data.

19 Claims, 29 Drawing Sheets

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl" (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 0.00 | 1.44 | 0.01 | 0.69 | 0.00 | 0.0 | 39.79 | -0.77 | 2.20 | 0.01 | 1.062 | 66.4 | 42.8 | 0.21 | 20.65 |
| 0.02 | 1.44 | 0.02 | 0.69 | 0.01 | 0.8 | 39.77 | -1.53 | 2.20 | 0.03 | 1.06 | 66.3 | 42.8 | 0.62 | 20.63 |
| 0.04 | 1.44 | 0.03 | 0.69 | 0.03 | 1.6 | 39.74 | -2.29 | 2.20 | 0.05 | 1.06 | 66.3 | 42.8 | 1.03 | 20.60 |
| 0.06 | 1.44 | 0.05 | 0.69 | 0.04 | 2.4 | 39.69 | -3.05 | 2.20 | 0.07 | 1.06 | 66.3 | 42.9 | 1.44 | 20.56 |
| 0.08 | 1.44 | 0.06 | 0.69 | 0.06 | 3.2 | 39.63 | -3.80 | 2.21 | 0.10 | 1.06 | 66.3 | 42.9 | 1.86 | 20.50 |
| 0.10 | 1.44 | 0.08 | 0.69 | 0.07 | 4.0 | 39.56 | -4.54 | 2.21 | 0.12 | 1.05 | 66.2 | 42.9 | 2.27 | 20.44 |
| 0.12 | 1.44 | 0.09 | 0.68 | 0.08 | 4.8 | 39.47 | -5.27 | 2.21 | 0.14 | 1.05 | 66.2 | 43.0 | 2.67 | 20.36 |
| 0.14 | 1.44 | 0.10 | 0.68 | 0.10 | 5.6 | 39.36 | -5.99 | 2.21 | 0.16 | 1.05 | 66.1 | 43.0 | 3.08 | 20.28 |
| 0.16 | 1.45 | 0.12 | 0.68 | 0.11 | 6.3 | 39.24 | -6.70 | 2.22 | 0.18 | 1.04 | 66.0 | 43.1 | 3.49 | 20.18 |
| 0.18 | 1.45 | 0.13 | 0.67 | 0.12 | 7.1 | 39.11 | -7.39 | 2.22 | 0.20 | 1.04 | 65.9 | 43.2 | 3.89 | 20.07 |
| 0.20 | 1.45 | 0.14 | 0.67 | 0.14 | 7.9 | 38.96 | -8.06 | 2.22 | 0.22 | 1.03 | 65.9 | 43.2 | 4.29 | 19.95 |
| 0.22 | 1.46 | 0.16 | 0.67 | 0.15 | 8.7 | 38.80 | -8.72 | 2.23 | 0.24 | 1.02 | 65.7 | 43.3 | 4.69 | 19.82 |

FIG. 24A

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl'' (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 0.24 | 1.46 | 0.17 | 0.66 | 0.17 | 9.5 | 38.62 | -9.36 | 2.23 | 0.26 | 1.01 | 65.6 | 43.4 | 5.09 | 19.68 |
| 0.26 | 1.46 | 0.18 | 0.66 | 0.18 | 10.2 | 38.44 | -9.98 | 2.24 | 0.28 | 1.00 | 65.5 | 43.5 | 5.48 | 19.53 |
| 0.28 | 1.47 | 0.20 | 0.65 | 0.19 | 11.0 | 38.24 | -10.57 | 2.24 | 0.30 | 1.00 | 65.4 | 43.6 | 5.87 | 19.38 |
| 0.30 | 1.47 | 0.21 | 0.65 | 0.21 | 11.8 | 38.03 | -11.15 | 2.25 | 0.32 | 0.99 | 65.2 | 43.7 | 6.26 | 19.21 |
| 0.32 | 1.48 | 0.22 | 0.64 | 0.22 | 12.5 | 37.80 | -11.70 | 2.26 | 0.34 | 0.98 | 65.1 | 43.9 | 6.64 | 19.04 |
| 0.34 | 1.48 | 0.24 | 0.63 | 0.23 | 13.3 | 37.57 | -12.24 | 2.26 | 0.36 | 0.97 | 64.9 | 44.0 | 7.02 | 18.86 |
| 0.36 | 1.48 | 0.25 | 0.63 | 0.24 | 14.0 | 37.32 | -12.74 | 2.27 | 0.38 | 0.96 | 64.8 | 44.1 | 7.40 | 18.67 |
| 0.38 | 1.49 | 0.26 | 0.62 | 0.26 | 14.8 | 37.07 | -13.23 | 2.28 | 0.40 | 0.95 | 64.6 | 44.3 | 7.77 | 18.47 |
| 0.40 | 1.49 | 0.27 | 0.61 | 0.27 | 15.5 | 36.80 | -13.69 | 2.29 | 0.42 | 0.94 | 64.4 | 44.4 | 8.14 | 18.27 |
| 0.42 | 1.49 | 0.29 | 0.61 | 0.28 | 16.3 | 36.53 | -14.12 | 2.29 | 0.44 | 0.93 | 64.2 | 44.6 | 8.51 | 18.07 |
| 0.44 | 1.50 | 0.30 | 0.60 | 0.30 | 17.0 | 36.25 | -14.53 | 2.30 | 0.46 | 0.92 | 64.0 | 44.8 | 8.87 | 17.85 |
| 0.46 | 1.51 | 0.31 | 0.59 | 0.31 | 17.7 | 35.96 | -14.92 | 2.31 | 0.47 | 0.91 | 63.8 | 45.0 | 9.23 | 17.63 |

FIG. 24B

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl" (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 0.48 | 1.52 | 0.32 | 0.59 | 0.32 | 18.4 | 35.66 | -15.28 | 2.32 | 0.49 | 0.90 | 63.6 | 45.1 | 9.58 | 17.41 |
| 0.50 | 1.52 | 0.33 | 0.58 | 0.33 | 19.1 | 35.35 | -15.62 | 2.33 | 0.51 | 0.88 | 63.4 | 45.3 | 9.93 | 17.18 |
| 0.52 | 1.53 | 0.35 | 0.57 | 0.35 | 19.9 | 35.04 | -15.93 | 2.34 | 0.53 | 0.87 | 63.2 | 45.5 | 10.27 | 16.95 |
| 0.54 | 1.54 | 0.36 | 0.56 | 0.36 | 20.6 | 34.72 | -16.21 | 2.35 | 0.55 | 0.86 | 62.9 | 45.7 | 10.61 | 16.72 |
| 0.56 | 1.55 | 0.37 | 0.55 | 0.37 | 21.3 | 34.40 | -16.48 | 2.36 | 0.56 | 0.85 | 62.7 | 46.0 | 10.95 | 16.48 |
| 0.58 | 1.55 | 0.38 | 0.55 | 0.38 | 21.9 | 34.07 | -16.72 | 2.37 | 0.58 | 0.84 | 62.5 | 46.2 | 11.28 | 16.24 |
| 0.60 | 1.56 | 0.39 | 0.54 | 0.39 | 22.6 | 33.73 | -16.93 | 2.39 | 0.60 | 0.82 | 62.2 | 46.4 | 11.60 | 16.00 |
| 0.62 | 1.57 | 0.40 | 0.53 | 0.41 | 23.3 | 33.40 | -17.12 | 2.40 | 0.61 | 0.81 | 62.0 | 46.6 | 11.92 | 15.76 |
| 0.64 | 1.58 | 0.41 | 0.52 | 0.42 | 24.0 | 33.05 | -17.30 | 2.41 | 0.63 | 0.80 | 61.7 | 46.9 | 12.24 | 15.52 |
| 0.66 | 1.58 | 0.42 | 0.51 | 0.43 | 24.6 | 32.71 | -17.45 | 2.42 | 0.65 | 0.79 | 61.4 | 47.1 | 12.55 | 15.27 |
| 0.68 | 1.59 | 0.43 | 0.51 | 0.44 | 25.3 | 32.36 | -17.57 | 2.44 | 0.66 | 0.77 | 61.2 | 47.4 | 12.85 | 15.03 |
| 0.70 | 1.60 | 0.44 | 0.50 | 0.45 | 25.9 | 32.01 | -17.68 | 2.45 | 0.68 | 0.76 | 60.9 | 47.6 | 13.15 | 14.78 |

FIG. 24C

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl'' (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 0.72 | 1.61 | 0.45 | 0.49 | 0.46 | 26.6 | 31.65 | -17.77 | 2.46 | 0.69 | 0.75 | 60.6 | 47.9 | 13.45 | 14.53 |
| 0.74 | 1.62 | 0.46 | 0.48 | 0.47 | 27.2 | 31.30 | -17.84 | 2.48 | 0.71 | 0.73 | 60.4 | 48.2 | 13.74 | 14.29 |
| 0.76 | 1.63 | 0.47 | 0.47 | 0.49 | 27.8 | 30.94 | -17.89 | 2.49 | 0.72 | 0.72 | 60.1 | 48.4 | 14.02 | 14.04 |
| 0.78 | 1.64 | 0.48 | 0.46 | 0.50 | 28.4 | 30.58 | -17.93 | 2.50 | 0.74 | 0.71 | 59.8 | 48.7 | 14.31 | 13.80 |
| 0.80 | 1.65 | 0.49 | 0.46 | 0.51 | 29.1 | 30.23 | -17.94 | 2.52 | 0.75 | 0.70 | 59.5 | 49.0 | 14.58 | 13.55 |
| 0.82 | 1.66 | 0.50 | 0.45 | 0.52 | 29.7 | 29.87 | -17.94 | 2.53 | 0.76 | 0.68 | 59.2 | 49.3 | 14.85 | 13.31 |
| 0.84 | 1.67 | 0.51 | 0.44 | 0.53 | 30.3 | 29.51 | -17.93 | 2.55 | 0.78 | 0.67 | 58.9 | 49.6 | 15.12 | 13.07 |
| 0.86 | 1.68 | 0.52 | 0.43 | 0.54 | 30.8 | 29.15 | -17.90 | 2.57 | 0.79 | 0.66 | 58.6 | 49.9 | 15.38 | 12.83 |
| 0.88 | 1.69 | 0.53 | 0.42 | 0.55 | 31.4 | 28.79 | -17.86 | 2.58 | 0.80 | 0.65 | 58.3 | 50.2 | 15.64 | 12.59 |
| 0.90 | 1.70 | 0.53 | 0.42 | 0.56 | 32.0 | 28.43 | -17.80 | 2.60 | 0.82 | 0.64 | 58.0 | 50.5 | 15.89 | 12.36 |
| 0.92 | 1.71 | 0.54 | 0.41 | 0.57 | 32.6 | 28.08 | -17.74 | 2.61 | 0.83 | 0.62 | 57.7 | 50.8 | 16.14 | 12.13 |
| 0.94 | 1.72 | 0.55 | 0.40 | 0.58 | 33.1 | 27.72 | -17.66 | 2.63 | 0.84 | 0.61 | 57.4 | 51.1 | 16.38 | 11.90 |

FIG. 24D

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl" (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 0.96 | 1.73 | 0.56 | 0.39 | 0.59 | 33.7 | 27.37 | -17.57 | 2.65 | 0.85 | 0.60 | 57.1 | 51.5 | 16.62 | 11.67 |
| 0.98 | 1.74 | 0.57 | 0.38 | 0.60 | 34.2 | 27.02 | -17.47 | 2.66 | 0.87 | 0.59 | 56.8 | 51.8 | 16.85 | 11.45 |
| 1.00 | 1.75 | 0.57 | 0.38 | 0.61 | 34.8 | 26.67 | -17.36 | 2.68 | 0.88 | 0.58 | 56.5 | 52.1 | 17.08 | 11.22 |
| 1.02 | 1.76 | 0.58 | 0.37 | 0.62 | 35.3 | 26.32 | -17.24 | 2.70 | 0.89 | 0.57 | 56.2 | 52.5 | 17.30 | 11.00 |
| 1.04 | 1.78 | 0.59 | 0.36 | 0.63 | 35.8 | 25.98 | -17.11 | 2.72 | 0.90 | 0.55 | 55.8 | 52.8 | 17.52 | 10.79 |
| 1.06 | 1.79 | 0.60 | 0.36 | 0.63 | 36.4 | 25.64 | -16.98 | 2.73 | 0.91 | 0.54 | 55.5 | 53.2 | 17.74 | 10.58 |
| 1.08 | 1.80 | 0.60 | 0.35 | 0.64 | 36.9 | 25.30 | -16.83 | 2.75 | 0.92 | 0.53 | 55.2 | 53.5 | 17.95 | 10.37 |
| 1.10 | 1.81 | 0.61 | 0.34 | 0.65 | 37.4 | 24.96 | -16.69 | 2.77 | 0.93 | 0.52 | 54.9 | 53.9 | 18.16 | 10.16 |
| 1.12 | 1.82 | 0.62 | 0.33 | 0.66 | 37.9 | 24.63 | -16.53 | 2.79 | 0.94 | 0.51 | 54.6 | 54.3 | 18.36 | 9.95 |
| 1.14 | 1.84 | 0.62 | 0.33 | 0.67 | 38.4 | 24.29 | -16.37 | 2.81 | 0.95 | 0.50 | 54.3 | 54.6 | 18.56 | 9.75 |
| 1.16 | 1.85 | 0.63 | 0.32 | 0.68 | 38.9 | 23.97 | -16.21 | 2.83 | 0.96 | 0.49 | 54.0 | 55.0 | 18.75 | 9.56 |
| 1.18 | 1.86 | 0.64 | 0.31 | 0.69 | 39.3 | 23.64 | -16.04 | 2.85 | 0.97 | 0.48 | 53.6 | 55.4 | 18.95 | 9.36 |

FIG. 24E

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl'' (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 1.20 | 1.87 | 0.64 | 0.31 | 0.69 | 39.8 | 23.32 | -15.87 | 2.87 | 0.98 | 0.47 | 53.3 | 55.7 | 19.13 | 9.17 |
| 1.22 | 1.89 | 0.65 | 0.30 | 0.70 | 40.3 | 23.00 | -15.69 | 2.89 | 0.99 | 0.46 | 53.0 | 56.1 | 19.32 | 8.99 |
| 1.24 | 1.90 | 0.66 | 0.30 | 0.71 | 40.7 | 22.69 | -15.51 | 2.91 | 1.00 | 0.45 | 52.7 | 56.5 | 19.50 | 8.80 |
| 1.26 | 1.91 | 0.66 | 0.29 | 0.72 | 41.2 | 22.38 | -15.33 | 2.93 | 1.01 | 0.44 | 52.4 | 56.9 | 19.67 | 8.62 |
| 1.28 | 1.93 | 0.67 | 0.28 | 0.73 | 41.6 | 22.07 | -15.14 | 2.95 | 1.02 | 0.43 | 52.1 | 57.3 | 19.84 | 8.45 |
| 1.30 | 1.94 | 0.67 | 0.28 | 0.73 | 42.1 | 21.77 | -14.96 | 2.97 | 1.03 | 0.43 | 51.8 | 57.7 | 20.01 | 8.27 |
| 1.32 | 1.95 | 0.68 | 0.27 | 0.74 | 42.5 | 21.47 | -14.77 | 2.99 | 1.04 | 0.42 | 51.5 | 58.1 | 20.18 | 8.10 |
| 1.34 | 1.97 | 0.68 | 0.27 | 0.75 | 42.9 | 21.18 | -14.58 | 3.01 | 1.05 | 0.41 | 51.2 | 58.5 | 20.34 | 7.94 |
| 1.36 | 1.98 | 0.69 | 0.26 | 0.76 | 43.4 | 20.89 | -14.39 | 3.03 | 1.05 | 0.40 | 50.8 | 58.9 | 20.50 | 7.77 |
| 1.38 | 1.99 | 0.69 | 0.26 | 0.76 | 43.8 | 20.60 | -14.20 | 3.05 | 1.06 | 0.39 | 50.5 | 59.3 | 20.66 | 7.61 |
| 1.40 | 2.01 | 0.70 | 0.25 | 0.77 | 44.2 | 20.31 | -14.01 | 3.07 | 1.07 | 0.38 | 50.2 | 59.7 | 20.81 | 7.46 |
| 1.42 | 2.02 | 0.70 | 0.25 | 0.78 | 44.6 | 20.03 | -13.82 | 3.09 | 1.08 | 0.38 | 49.9 | 60.1 | 20.96 | 7.30 |

FIG. 24F

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl" (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 1.44 | 2.04 | 0.71 | 0.24 | 0.79 | 45.0 | 19.76 | -13.62 | 3.11 | 1.09 | 0.37 | 49.6 | 60.6 | 21.10 | 7.15 |
| 1.46 | 2.05 | 0.71 | 0.24 | 0.79 | 45.4 | 19.48 | -13.43 | 3.14 | 1.09 | 0.36 | 49.3 | 61.0 | 21.25 | 7.00 |
| 1.48 | 2.06 | 0.72 | 0.23 | 0.80 | 45.8 | 19.22 | -13.24 | 3.16 | 1.10 | 0.35 | 49.0 | 61.4 | 21.39 | 6.86 |
| 1.50 | 2.08 | 0.72 | 0.23 | 0.81 | 46.2 | 18.95 | -13.05 | 3.18 | 1.11 | 0.35 | 48.7 | 61.8 | 21.52 | 6.72 |
| 1.52 | 2.09 | 0.73 | 0.22 | 0.81 | 46.5 | 18.69 | -12.86 | 3.20 | 1.11 | 0.34 | 48.4 | 62.3 | 21.66 | 6.58 |
| 1.54 | 2.11 | 0.73 | 0.22 | 0.82 | 46.9 | 18.43 | -12.67 | 3.22 | 1.12 | 0.33 | 48.1 | 62.7 | 21.79 | 6.45 |
| 1.56 | 2.12 | 0.74 | 0.21 | 0.83 | 47.3 | 18.18 | -12.48 | 3.25 | 1.13 | 0.32 | 47.8 | 63.1 | 21.92 | 6.31 |
| 1.58 | 2.14 | 0.74 | 0.21 | 0.83 | 47.7 | 17.93 | -12.30 | 3.27 | 1.13 | 0.32 | 47.5 | 63.6 | 22.04 | 6.18 |
| 1.60 | 2.15 | 0.75 | 0.20 | 0.84 | 48.0 | 17.68 | -12.11 | 3.29 | 1.14 | 0.31 | 47.2 | 64.0 | 22.17 | 6.06 |
| 1.62 | 2.17 | 0.75 | 0.20 | 0.84 | 48.4 | 17.44 | -11.93 | 3.32 | 1.15 | 0.31 | 47.0 | 64.5 | 22.29 | 5.93 |
| 1.64 | 2.18 | 0.75 | 0.20 | 0.85 | 48.7 | 17.20 | -11.75 | 3.34 | 1.15 | 0.30 | 46.7 | 64.9 | 22.41 | 5.81 |
| 1.66 | 2.20 | 0.76 | 0.19 | 0.86 | 49.1 | 16.97 | -11.57 | 3.36 | 1.16 | 0.29 | 46.4 | 65.4 | 22.52 | 5.69 |

FIG. 24G

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl'' (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 1.68 | 2.21 | 0.76 | 0.19 | 0.86 | 49.4 | 16.74 | -11.39 | 3.38 | 1.16 | 0.29 | 46.1 | 65.8 | 22.64 | 5.58 |
| 1.70 | 2.23 | 0.76 | 0.18 | 0.87 | 49.7 | 16.51 | -11.21 | 3.41 | 1.17 | 0.28 | 45.8 | 66.3 | 22.75 | 5.46 |
| 1.72 | 2.24 | 0.77 | 0.18 | 0.87 | 50.1 | 16.28 | -11.03 | 3.43 | 1.18 | 0.28 | 45.5 | 66.7 | 22.86 | 5.35 |
| 1.74 | 2.26 | 0.77 | 0.18 | 0.88 | 50.4 | 16.06 | -10.86 | 3.45 | 1.18 | 0.27 | 45.3 | 67.2 | 22.97 | 5.24 |
| 1.76 | 2.27 | 0.78 | 0.17 | 0.89 | 50.7 | 15.85 | -10.69 | 3.48 | 1.19 | 0.26 | 45.0 | 67.6 | 23.07 | 5.14 |
| 1.78 | 2.29 | 0.78 | 0.17 | 0.89 | 51.0 | 15.63 | -10.52 | 3.50 | 1.19 | 0.26 | 44.7 | 68.1 | 23.17 | 5.04 |
| 1.80 | 2.31 | 0.78 | 0.17 | 0.90 | 51.3 | 15.42 | -10.35 | 3.53 | 1.20 | 0.25 | 44.4 | 68.6 | 23.27 | 4.93 |
| 1.82 | 2.32 | 0.79 | 0.16 | 0.90 | 51.6 | 15.22 | -10.19 | 3.55 | 1.20 | 0.25 | 44.2 | 69.0 | 23.37 | 4.84 |
| 1.84 | 2.34 | 0.79 | 0.16 | 0.91 | 52.0 | 15.01 | -10.02 | 3.57 | 1.21 | 0.24 | 43.9 | 69.5 | 23.47 | 4.74 |
| 1.86 | 2.35 | 0.79 | 0.16 | 0.91 | 52.3 | 14.81 | -9.86 | 3.60 | 1.21 | 0.24 | 43.6 | 70.0 | 23.56 | 4.64 |
| 1.88 | 2.37 | 0.80 | 0.15 | 0.92 | 52.5 | 14.61 | -9.71 | 3.62 | 1.22 | 0.23 | 43.4 | 70.4 | 23.66 | 4.55 |
| 1.90 | 2.38 | 0.80 | 0.15 | 0.92 | 52.8 | 14.42 | -9.55 | 3.65 | 1.22 | 0.23 | 43.1 | 70.9 | 23.75 | 4.46 |

FIG. 24H

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl'' (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 1.92 | 2.40 | 0.80 | 0.15 | 0.93 | 53.1 | 14.23 | -9.40 | 3.67 | 1.23 | 0.22 | 42.8 | 71.4 | 23.84 | 4.37 |
| 1.94 | 2.42 | 0.80 | 0.14 | 0.93 | 53.4 | 14.04 | -9.24 | 3.70 | 1.23 | 0.22 | 42.6 | 71.9 | 23.93 | 4.29 |
| 1.96 | 2.43 | 0.81 | 0.14 | 0.94 | 53.7 | 13.86 | -9.09 | 3.72 | 1.23 | 0.22 | 42.3 | 72.3 | 24.01 | 4.20 |
| 1.98 | 2.45 | 0.81 | 0.14 | 0.94 | 54.0 | 13.67 | -8.95 | 3.74 | 1.24 | 0.21 | 42.1 | 72.8 | 24.09 | 4.12 |
| 2.00 | 2.46 | 0.81 | 0.14 | 0.95 | 54.2 | 13.50 | -8.80 | 3.77 | 1.24 | 0.21 | 41.8 | 73.3 | 24.18 | 4.04 |
| 2.02 | 2.48 | 0.82 | 0.13 | 0.95 | 54.5 | 13.32 | -8.66 | 3.79 | 1.25 | 0.20 | 41.6 | 73.8 | 24.26 | 3.96 |
| 2.04 | 2.50 | 0.82 | 0.13 | 0.96 | 54.8 | 13.15 | -8.52 | 3.82 | 1.25 | 0.20 | 41.3 | 74.3 | 24.34 | 3.88 |
| 2.06 | 2.51 | 0.82 | 0.13 | 0.96 | 55.0 | 12.98 | -8.38 | 3.84 | 1.26 | 0.20 | 41.1 | 74.8 | 24.42 | 3.81 |
| 2.08 | 2.53 | 0.82 | 0.13 | 0.97 | 55.3 | 12.81 | -8.24 | 3.87 | 1.26 | 0.19 | 40.8 | 75.2 | 24.49 | 3.74 |
| 2.10 | 2.55 | 0.83 | 0.12 | 0.97 | 55.6 | 12.64 | -8.11 | 3.89 | 1.26 | 0.19 | 40.6 | 75.7 | 24.57 | 3.66 |
| 2.12 | 2.56 | 0.83 | 0.12 | 0.97 | 55.8 | 12.48 | -7.98 | 3.92 | 1.27 | 0.18 | 40.3 | 76.2 | 24.64 | 3.59 |
| 2.14 | 2.58 | 0.83 | 0.12 | 0.98 | 56.1 | 12.32 | -7.85 | 3.95 | 1.27 | 0.18 | 40.1 | 76.7 | 24.71 | 3.53 |

FIG. 24I

| Path Dist (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl" (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 2.16 | 2.60 | 0.83 | 0.12 | 0.98 | 56.3 | 12.16 | -7.72 | 3.97 | 1.27 | 0.18 | 39.9 | 77.2 | 24.78 | 3.46 |
| 2.18 | 2.61 | 0.84 | 0.11 | 0.99 | 56.6 | 12.01 | -7.60 | 4.00 | 1.28 | 0.17 | 39.6 | 77.7 | 24.85 | 3.39 |
| 2.20 | 2.63 | 0.84 | 0.11 | 0.99 | 56.8 | 11.86 | -7.47 | 4.02 | 1.28 | 0.17 | 39.4 | 78.2 | 24.92 | 3.33 |
| 2.22 | 2.65 | 0.84 | 0.11 | 1.00 | 57.0 | 11.71 | -7.35 | 4.05 | 1.28 | 0.17 | 39.2 | 78.7 | 24.99 | 3.27 |
| 2.24 | 2.66 | 0.84 | 0.11 | 1.00 | 57.3 | 11.56 | -7.23 | 4.07 | 1.29 | 0.16 | 38.9 | 79.2 | 25.05 | 3.20 |
| 2.26 | 2.68 | 0.84 | 0.11 | 1.00 | 57.5 | 11.42 | -7.11 | 4.10 | 1.29 | 0.16 | 38.7 | 79.7 | 25.11 | 3.15 |
| 2.28 | 2.70 | 0.85 | 0.10 | 1.01 | 57.7 | 11.27 | -7.00 | 4.12 | 1.29 | 0.16 | 38.5 | 80.2 | 25.18 | 3.09 |
| 2.30 | 2.71 | 0.85 | 0.10 | 1.01 | 57.9 | 11.13 | -6.89 | 4.15 | 1.30 | 0.16 | 38.3 | 80.7 | 25.24 | 3.03 |
| 2.32 | 2.73 | 0.85 | 0.10 | 1.02 | 58.2 | 11.00 | -6.78 | 4.18 | 1.30 | 0.15 | 38.0 | 81.2 | 25.30 | 2.97 |
| 2.34 | 2.75 | 0.85 | 0.10 | 1.02 | 58.4 | 10.86 | -6.67 | 4.20 | 1.30 | 0.15 | 37.8 | 81.7 | 25.36 | 2.92 |
| 2.36 | 2.76 | 0.85 | 0.10 | 1.02 | 58.6 | 10.73 | -6.56 | 4.23 | 1.31 | 0.15 | 37.6 | 82.2 | 25.42 | 2.87 |
| 2.38 | 2.78 | 0.86 | 0.09 | 1.03 | 58.8 | 10.60 | -6.45 | 4.25 | 1.31 | 0.14 | 37.4 | 82.7 | 25.48 | 2.81 |

FIG. 24J

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl'' (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 2.40 | 2.80 | 0.86 | 0.09 | 1.03 | 59.0 | 10.47 | -6.35 | 4.28 | 1.31 | 0.14 | 37.2 | 83.2 | 25.53 | 2.76 |
| 2.42 | 2.82 | 0.86 | 0.09 | 1.03 | 59.2 | 10.34 | -6.25 | 4.31 | 1.32 | 0.14 | 37.0 | 83.8 | 25.59 | 2.71 |
| 2.44 | 2.83 | 0.86 | 0.09 | 1.04 | 59.5 | 10.22 | -6.15 | 4.33 | 1.32 | 0.14 | 36.8 | 84.3 | 25.64 | 2.66 |
| 2.46 | 2.85 | 0.86 | 0.09 | 1.04 | 59.7 | 10.09 | -6.05 | 4.36 | 1.32 | 0.13 | 36.6 | 84.8 | 25.69 | 2.62 |
| 2.48 | 2.87 | 0.87 | 0.09 | 1.04 | 59.9 | 9.97 | -5.95 | 4.39 | 1.32 | 0.13 | 36.3 | 85.3 | 25.75 | 2.57 |
| 2.50 | 2.89 | 0.87 | 0.08 | 1.05 | 60.1 | 9.85 | -5.86 | 4.41 | 1.33 | 0.13 | 36.1 | 85.8 | 25.80 | 2.52 |
| 2.52 | 2.90 | 0.87 | 0.08 | 1.05 | 60.3 | 9.74 | -5.77 | 4.44 | 1.33 | 0.13 | 35.9 | 86.3 | 25.85 | 2.48 |
| 2.54 | 2.92 | 0.87 | 0.08 | 1.06 | 60.4 | 9.62 | -5.68 | 4.47 | 1.33 | 0.13 | 35.7 | 86.8 | 25.90 | 2.43 |
| 2.56 | 2.94 | 0.87 | 0.08 | 1.06 | 60.6 | 9.51 | -5.59 | 4.49 | 1.33 | 0.12 | 35.5 | 87.4 | 25.95 | 2.39 |
| 2.58 | 2.95 | 0.87 | 0.08 | 1.06 | 60.8 | 9.40 | -5.50 | 4.52 | 1.33 | 0.12 | 35.3 | 87.9 | 25.99 | 2.35 |
| 2.60 | 2.97 | 0.88 | 0.08 | 1.07 | 61.0 | 9.29 | -5.41 | 4.55 | 1.34 | 0.12 | 35.2 | 88.4 | 26.04 | 2.31 |
| 2.62 | 2.99 | 0.88 | 0.08 | 1.07 | 61.2 | 9.18 | -5.33 | 4.57 | 1.34 | 0.12 | 35.0 | 88.9 | 26.09 | 2.27 |

FIG. 24K

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl'' (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 2.64 | 3.01 | 0.88 | 0.07 | 1.07 | 61.4 | 9.07 | -5.24 | 4.60 | 1.34 | 0.11 | 34.8 | 89.4 | 26.13 | 2.23 |
| 2.66 | 3.02 | 0.88 | 0.07 | 1.07 | 61.6 | 8.97 | -5.16 | 4.63 | 1.35 | 0.11 | 34.6 | 90.0 | 26.18 | 2.19 |
| 2.68 | 3.04 | 0.88 | 0.07 | 1.07 | 61.8 | 8.86 | -5.08 | 4.65 | 1.35 | 0.11 | 34.4 | 90.5 | 26.22 | 2.15 |
| 2.70 | 3.06 | 0.88 | 0.07 | 1.08 | 61.9 | 8.76 | -5.00 | 4.68 | 1.35 | 0.11 | 34.2 | 91.0 | 26.26 | 2.12 |
| 2.72 | 3.08 | 0.88 | 0.07 | 1.08 | 62.1 | 8.66 | -4.93 | 4.71 | 1.35 | 0.11 | 34.0 | 91.5 | 26.31 | 2.08 |
| 2.74 | 3.10 | 0.89 | 0.07 | 1.08 | 62.3 | 8.56 | -4.85 | 4.73 | 1.36 | 0.11 | 33.8 | 92.1 | 26.35 | 2.04 |
| 2.76 | 3.11 | 0.89 | 0.07 | 1.09 | 62.4 | 8.47 | -4.77 | 4.76 | 1.36 | 0.10 | 33.7 | 92.6 | 26.39 | 2.01 |
| 2.78 | 3.13 | 0.89 | 0.07 | 1.09 | 62.6 | 8.37 | -4.70 | 4.79 | 1.36 | 0.10 | 33.5 | 93.1 | 26.43 | 1.98 |
| 2.80 | 3.15 | 0.89 | 0.07 | 1.09 | 62.8 | 8.28 | -4.63 | 4.82 | 1.36 | 0.10 | 33.3 | 93.6 | 26.47 | 1.94 |
| 2.82 | 3.17 | 0.89 | 0.06 | 1.10 | 62.9 | 8.18 | -4.56 | 4.84 | 1.36 | 0.10 | 33.1 | 94.2 | 26.51 | 1.91 |
| 2.84 | 3.18 | 0.89 | 0.06 | 1.10 | 63.1 | 8.09 | -4.49 | 4.87 | 1.37 | 0.10 | 32.9 | 94.7 | 26.55 | 1.88 |
| 2.86 | 3.20 | 0.89 | 0.06 | 1.10 | 63.3 | 8.00 | -4.42 | 4.90 | 1.37 | 0.10 | 32.8 | 95.2 | 26.58 | 1.85 |

FIG. 24L

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl'' (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 2.88 | 3.22 | 0.90 | 0.06 | 1.11 | 63.4 | 7.91 | -4.35 | 4.93 | 1.37 | 0.09 | 32.6 | 95.8 | 26.62 | 1.82 |
| 2.90 | 3.24 | 0.90 | 0.06 | 1.11 | 63.6 | 7.83 | -4.29 | 4.95 | 1.37 | 0.09 | 32.4 | 96.3 | 26.66 | 1.79 |
| 2.92 | 3.26 | 0.90 | 0.06 | 1.11 | 63.7 | 7.74 | -4.22 | 4.98 | 1.37 | 0.09 | 32.3 | 96.8 | 26.69 | 1.76 |
| 2.94 | 3.27 | 0.90 | 0.06 | 1.12 | 63.9 | 7.66 | -4.16 | 5.01 | 1.37 | 0.09 | 32.1 | 97.4 | 26.73 | 1.73 |
| 2.96 | 3.29 | 0.90 | 0.06 | 1.12 | 64.1 | 7.57 | -4.10 | 5.03 | 1.38 | 0.09 | 31.9 | 97.9 | 26.76 | 1.70 |
| 2.98 | 3.31 | 0.90 | 0.06 | 1.12 | 64.2 | 7.49 | -4.04 | 5.06 | 1.38 | 0.09 | 31.8 | 98.4 | 26.80 | 1.67 |
| 3.00 | 3.33 | 0.90 | 0.06 | 1.12 | 64.4 | 7.41 | -3.98 | 5.09 | 1.38 | 0.08 | 31.6 | 99.0 | 26.83 | 1.65 |
| 3.02 | 3.35 | 0.90 | 0.05 | 1.13 | 64.5 | 7.33 | -3.92 | 5.12 | 1.38 | 0.08 | 31.4 | 99.5 | 26.86 | 1.62 |
| 3.04 | 3.36 | 0.90 | 0.05 | 1.13 | 64.7 | 7.25 | -3.86 | 5.15 | 1.38 | 0.08 | 31.3 | 100.0 | 26.89 | 1.59 |
| 3.06 | 3.38 | 0.91 | 0.05 | 1.13 | 64.8 | 7.18 | -3.80 | 5.17 | 1.38 | 0.08 | 31.1 | 100.6 | 26.93 | 1.57 |
| 3.08 | 3.40 | 0.91 | 0.05 | 1.13 | 64.9 | 7.10 | -3.75 | 5.20 | 1.39 | 0.08 | 31.0 | 101.1 | 26.96 | 1.54 |
| 3.10 | 3.42 | 0.91 | 0.05 | 1.14 | 65.1 | 7.02 | -3.69 | 5.23 | 1.39 | 0.08 | 30.8 | 101.7 | 26.99 | 1.52 |

FIG. 24M

| Path Dis (m) | Center Dist (m) | Range Rate (m/s) | Range Acc (m/s²) | Head Angle (rad) | Head Angle (°) | Rot Rate (°/s) | Rot Acc (°/s²) | fl (mm) | fl' (mm/s) | fl'' (mm/s²) | Center Height (°) | Point Source Pos (mm) | Point Source Vel (mm/s) | Point Source Acc (mm/s²) |
|---|---|---|---|---|---|---|---|---|---|---|---|---|---|---|
| 3.12 | 3.44 | 0.91 | 0.05 | 1.14 | 65.2 | 6.95 | -3.64 | 5.26 | 1.39 | 0.08 | 30.6 | 102.2 | 27.02 | 1.50 |
| 3.14 | 3.45 | 0.91 | 0.05 | 1.14 | 65.4 | 6.88 | -3.59 | 5.28 | 1.39 | 0.08 | 30.5 | 102.7 | 27.05 | 1.47 |
| 3.16 | 3.47 | 0.91 | 0.05 | 1.14 | 65.5 | 6.81 | -3.53 | 5.31 | 1.39 | 0.07 | 30.3 | 103.3 | 27.08 | 1.45 |
| 3.18 | 3.49 | 0.91 | 0.05 | 1.15 | 65.6 | 6.74 | -3.48 | 5.34 | 1.39 | 0.07 | 30.2 | 103.8 | 27.11 | 1.43 |
| 3.20 | 3.51 | 0.91 | 0.05 | 1.15 | 65.8 | 6.67 | -3.43 | 5.37 | 1.40 | 0.07 | 30.0 | 104.4 | 27.14 | 1.41 |

FIG. 24N

SYSTEM AND METHODS FOR MONITORING AND ASSESSING MOBILITY

STATEMENT OF GOVERNMENT SUPPORT

This invention was made with United States Government support awarded by NSF Grant Number 1153572. The United States Government has certain rights in this invention.

CROSS REFERENCES TO RELATED APPLICATIONS

This application claims priority to U.S. Provisional Application No. 61/468,666, filed on Mar. 29, 2011, which is hereby incorporated by reference.

INTRODUCTION

Current trends in healthcare and rehabilitation reflect a growing need for tracking physical activity of individuals. Rehabilitation and physical therapy facilities, including assisted living residences, are expanding to address the needs of individuals, particularly the elderly. The U.S. Census Bureau projects that the population in the U.S. of people between the ages of 65 and 84 may increase by 38.8 percent by 2020, and the population of people over age 85 may increase by 18.7 percent. A universal method fails to exist that provides guidance in assessing mobility of an individual to reach a conclusion regarding, e.g., whether assisted living is needed.

BRIEF DESCRIPTION

A system and methods are provided for monitoring and assessing a subject's mobility. The system and methods relate generally to physical activity and suitably to tools for monitoring and assessing physical activity by capturing images of a subject's movement, including range of motion, gait, balance and activities of daily living at different time periods and comparing those images to stored data.

For purposes of this application, the terms "mobility" or "motion" or "motor skills" are used interchangeably and refer to movement including range of motion, gait, balance and activities of daily living. Furthermore, the term "subject" includes a human, animal, or any object. In one embodiment, known mobility data based on historical normalized data is compared to a subject's captured mobility data to determine whether the subject is performing above, below, or consistent with the normalized data. Normalized data may be, for example, based on population information or based on information that matches a profile of the subject. The profile of the subject may include, for example, height, weight, age, type of injury, sex, race, geographical area, etc. This information may be used to establish conclusions regarding the subject, for example, whether the subject may function independently or requires assistance.

In another embodiment, a subject's captured mobility data is compared with historical personal data of the subject to determine whether any change in the personal data has occurred. Personal data may include previous data recorded relative to the subject. This information may also be used to establish conclusions regarding the subject, for example, whether the subject may function independently or requires assistance. The conclusions with respect to personal data may be suitably combined with the normalized data to provide a more thorough assessment of the subject.

The system for monitoring and assessing mobility of a subject includes a stand component having a base member and a support member extending from the base member, and suitably includes a camera bar connected to the support member and distally opposed to the base. The camera bar suitably has a plurality of cameras mounted thereon, and may include a stereo camera and a color camera. One or more structured light projectors may also be mounted on the camera bar. The structured light projectors are operatively coupled to the subject being assessed and produce structured light coupled to the movement of the subject. The system may also include an overhead camera, as well as a foot-level camera. Also, the system may include a low resolution thermal imaging system or infrared spot detector for tracking the point skin temperature of a subject. In other embodiments, additional imaging and other equipment may be included and may be more distally opposed to the base member than the camera bar.

In another embodiment, the system may also include a control panel component connected to the support member that is juxtaposed between the base member and the camera bar. The control panel component suitably has a processor configured to communicate with the plurality of cameras and the structured light projectors to convert the structured light into mobility data of the subject. The processor further compares the mobility data of the subject to saved historical data in order to determine a level of mobility of the subject. The saved historical data may be normalized data or personal data.

BRIEF DESCRIPTION OF THE DRAWINGS

Embodiments described herein may be better understood and appreciated by reference to the detailed description presented herein in conjunction with the accompanying drawings of which:

FIGS. 24(A-N) depict focal length requirements for the baseline system.

DETAILED DESCRIPTION

Figure 1:
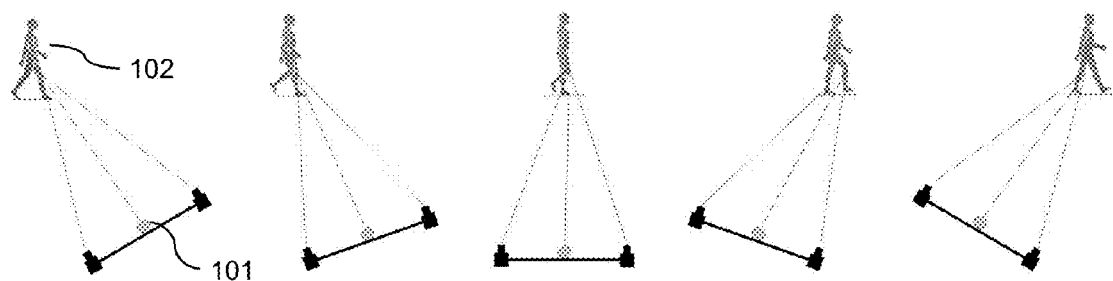
FIG. 1 illustrates an image capture performed by the mobility monitoring system described herein.

A mobility monitoring system and methods are provided for monitoring and assessing motion in a subject, for example, range of motion, gait, balance and simulated activities of daily living ("ADL"). The mobility monitoring system is an autonomous intelligent system developed to, at a minimum, measure the mobility of subjects over different time periods to assess changes. The system may further provide comparisons of a subject's mobility with established norms for a subject's gender or age group. The mobility monitoring system may archive mobility results to allow a subject to see his or her progression or regression over time.

Before any embodiments are explained in detail herein, however, it is to be understood that the embodiments are not limited in application to the details of construction and the arrangement of components, functions or processes set forth in the following description and illustrated in the following drawings. Such description and drawings are not intended to limit the scope of the embodiments described herein as set forth in the appended claims. Other embodiments may be practiced or carried out in various other ways.

Further, no admission is made that any reference, including any patent or patent document, cited in this specification constitutes prior art. In particular, it will be understood that, unless otherwise stated, reference to any document herein does not constitute an admission that any of these documents form part of the common general knowledge in the prior art in the United States or in any other country. Any discussion of the references states what their authors assert, and the applicant reserves the right to challenge the accuracy and pertinence of any of the documents cited herein.

Throughout this disclosure, various aspects of the methods and systems described herein may be presented in a range format. It should be understood that the description in range format is merely for convenience and brevity, and should not be construed as an inflexible limitation on the scope of the processes described herein. Accordingly, as will be understood by one skilled in the art, for any and all purposes, particularly in terms of providing a written description, all ranges disclosed herein also encompass any and all possible subranges and combinations of subranges thereof, as well as all integral and fractional numerical values within that range. As only one example, a range of 20% to 40% may be broken down into ranges of 20% to 32.5% and 32.5% to 40%, 20% to 27.5% and 27.5% to 40%, etc. Any listed range is also easily recognized as sufficiently describing and enabling the same range being broken down into at least equal halves, thirds, quarters, fifths, tenths, etc. As a non-limiting example, each range discussed herein may be readily broken down into a lower third, middle third, and upper third, etc. Further, as will also be understood by one skilled in the art, all language such as "up to," "at least," "greater than," "less than," "more than" and the like include the number recited and refer to ranges which may be subsequently broken down into subranges as discussed above. In the same manner, all ratios disclosed herein also include all subratios falling within the broader ratio. Further, the phrases "ranging/ranges between" a first indicate number and a second indicate number and "ranging/ranges from" a first indicate number "to" a second indicate number are used herein interchangeably. The foregoing are only examples of what is specifically intended.

Also, it is to be understood that the phraseology and terminology used herein is for the purpose of description and should not be regarded as limiting. The use of "comprising," "including," "having," and variations thereof herein is meant to encompass the items listed thereafter and equivalents thereof as well as additional items. "Comprising" encompasses the terms "consisting of" and "consisting essentially of." The use of "consisting essentially of" means that the composition or method may include additional ingredients and/or steps, but only if the additional ingredients and/or steps do not materially alter the basic and novel characteristics of the claimed composition or method. Unless specified or limited otherwise, the terms such as "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Unless otherwise noted, technical terms are used according to conventional usage. As used herein, certain definitions may be useful in aiding the skilled practitioner in understanding the embodiments described herein. For purposes of this application, the term "operator" or "user" refers to the entity operating the system. Other useful definitions are also given herein.

Figure 4:
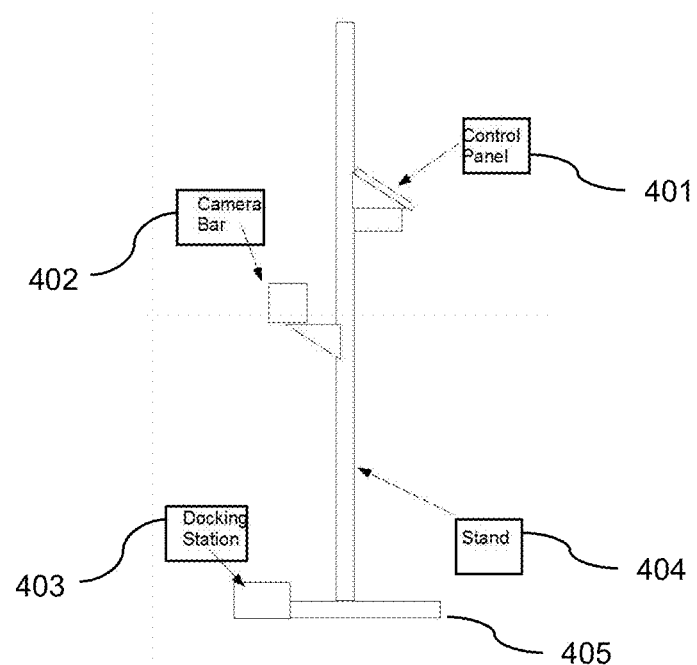
FIG. 4 illustrates main components of an embodiment of a mobility monitoring system.

It is envisioned that the mobility monitoring system may be readily set up and operated from any location, such as a physician's office or other healthcare facility, in a cost effective and space saving manner. One embodiment of the system will allow remote or autonomous operation for assessment in the subject's home or other facility. Accordingly, using a mobility monitoring system to run a mobility assessment may be readily applied to people needing such assessment, such as the elderly, as part of a routine healthcare examination. In the remote or autonomous mode of operation, it may be used to assess the status of subject's newly released from hospitals or track conditions of debilitating disease for reporting to a healthcare provider. FIG. 4 shows one embodiment of a mobility monitoring system. The mobility monitoring system includes a base 405, control panel 401, camera bar 402, and docking station 403.

The mobility monitoring system performs objective quantitative measurements that replace current techniques related to observational subjective testing, which requires too much judgment and presents opportunity for error. The mobility monitoring system performs objective quantitative measurements of a subject's mobility and associated characteristics, such as range of motion and ADL using computer vision, artificial intelligence and other computer algorithms. In many instances, the mobility monitoring system may inexpensively perform an assessment in a few minutes.

The mobility monitoring system monitors and assesses a variety of physical activities of a subject. For example, the mobility monitoring system may be utilized for rehabilitative assessments of a subject. Moreover, the mobility monitoring system may perform measurements and supervise ongoing physical therapy at a certain location. The mobility monitoring system may include additional functionality that allows processing of images to monitor an individual's vital signs including blood pressure, pulse rate and blood oxygen. A low resolution thermal imaging system or an infrared spot detector may be added to the system which further allows tracking of point skin temperature of a subject. The three-dimensional imagery captured by the system may also improve an assessment of wounds when the system is implemented in a close-up mode.

The mobility monitoring system may be used to expand frequent monitoring of several parameters of a subject, and process data pertaining to those parameters to generate an initial assessment of the subject. The data and initial assessment may then be transmitted to, for example, a healthcare facility or physician's office, which may reduce the number of office visits to a physician by the subject. Further, such transmissions may allow for diagnosis and for early identification of status changes, thus preventing hospitalization.

The mobility monitoring system is user-friendly, thereby allowing operation of the system without requiring extensive or specialized training. Furthermore, the mobility monitoring system may be operated in an autonomous mode for many applications. The mobility monitoring system may also be operated interactively such as with a remote healthcare professional.

Figure 2:
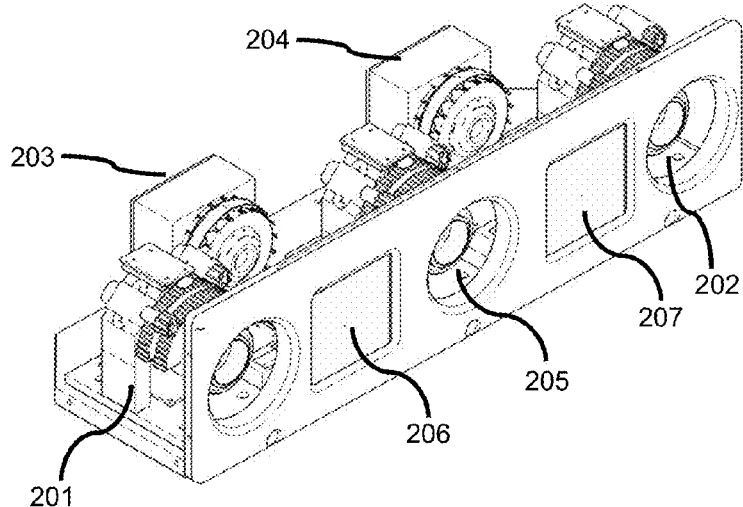
FIG. 2 illustrates an optical bench assembly of one embodiment of a mobility monitoring system.

In one embodiment, shown in FIG. 2, the mobility monitoring system includes multiple cameras 201 and 202, mounted on a tracker system equipped to follow the motion of a subject at a constant scale and collect data to quantitatively determine that motion. In the illustrated embodiment, a light source 101 maintains a constant pitch on the subject 102 and a tracker holds the subject's trunk at the center of a field of view as depicted in the sequence shown in FIG. 1. Stereo cameras 201 and 202 are able to find the same spot each time data is collected and measure the variations of local range. The embodiment may also include light sources 203 and 204, each placed near a camera. Each increases the baseline for the opposite camera, and thus, increases the accuracy of the depth. The individual measurement angles are determined with respect to the sources and the cameras and between the cameras, and combined using sensor fusion algorithms.

A camera bar 402 may provide support for the system's primary image acquisition components. The camera bar is suitably an optical bench that may include at least one or more camera assemblies 201, optionally also 202, and 205, and one or more structured or patterned light projectors 203, 204, 206, and 207.

Two stereo cameras 201 and 202 of the three camera assemblies operate using near-infrared ("NIR") technology to generate a stereo image from structured light projected on the subject by using infrared light from one or more projectors 203, 204, 206, and 207. The remaining camera assembly is a color camera 205. Each camera assembly 201, 202, and 205 includes a complementary metal-oxide-semiconductor ("CMOS") imaging sensor, a vari-focus lens, and zoom and focus motors. A structured light projector may include a point source 203 and a patterned film and positioning system 206 to maintain constant size on the subject The point source 203 includes multiple NIR light emitting diodes ("LED") operating in a simultaneously flashing pulsed mode in synchronization with the camera exposure time (i.e., shutter), an integrating sphere and a pinhole. The patterned film contains spots ranging, when projected, from one to two pixels in diameter. In one embodiment, two processor boards, one for the color camera 205 and one for the stereo cameras 201 and 202, are mounted on the optical bench structure.

In this specific embodiment, the stereo cameras use an Aptina MT9V034 CMOS sensor (Aptina, 2004). This sensor allows for agile image size that ranges up to 752×480 pixels, which are 6 μm square. The large pixel size increases the camera sensitivity over higher resolution cameras.

In the system, most applications may be of larger dimensions in the vertical direction or view. Hence, the camera is suitably rotated 90° which allows image sizes to 752 pixels in the vertical direction. At this image size, the selected cameras may operate at a nominal one hundred twenty frames per second ("fps"). Considering the maximum stride size, the gait and vertical balance is suitably imaged with a 1:2 aspect ratio of 314 horizontal by 628 vertical, which would allow approximately twice the frame rate. The 1:2 aspect ratio appears optimal, but other ratios may be suitable.

The color camera system uses an Aptina MT9T031 color CMOS sensor. The Aptina sensor is agile and has up to 2048 horizontal by 1536 vertical pixels, which form a 3.20 μm square. This is approximately ½ of the size of the NIR pixels. Hence, with slight scaling in the zoom, the color camera may have twice the resolution as the NIR cameras. The color sensor is able handle a high clock rate. With an image size of 628 horizontal by 1256 vertical pixels, it is able to operate at around 54 fps. At this image size, the color camera may operate at 30 fps. Each of the cameras is directly interfaced to a processor chip. A depth of field image from the stereo cameras is used to render a three dimensional (3D) image from the output of the color camera.

During analysis, a 3D computer model of the subject is built. This model may augment the color imagery, which may be rendered in 3D for an operator using a proper visual aid.

The system operates with minimal supervision, reducing the workload of operators such as healthcare professionals. The system may be installed in a home environment to perform monitoring of physical therapy or a prescribed regimen to assess recovery after hospital release, which may also reduce the need for a healthcare professional to visit a residence. Such monitoring may also reduce readmission to hospitals. The system reduces the data collected to a manageable form. The system has a touch panel control area which includes a minimal set of large and clear icons to set up for a given test. This minimal set of icons is selected to cover only those needed to perform a task at hand.

In one embodiment, the operator interface may be suitably designed using a smart phone software such as Android, or Qt, an open source tool. The motor skills data is processed via tools, such as OpenSim, to present the data in the expected clinical format.

Suitably, only a few icons are shown at any one time to facilitate ease of use of the system. For example, a greeting screen may be used which has icons of "Returning Person" and "New Person." The function occurring upon selection of these icons may be networked. For example, if the "Returning Person" icon is used, then the operator may have the subject's record available at the time of use of the system. An on-screen keyboard supplemented with autocompletion may allow the computer to automatically select the cited status by finding the patient's profile or finding no matching subject in the database, i.e., "New Person".

After a subject's profile is selected, the networked information may suitably contain the specific test that is recommended for the subject. If the recommendation is for a performance oriented assessment, then the functions may be set to perform a category of tests, such as Tinetti Scale, ADL, or other specific tests like "Balance" and "Gait." When a function is selected by the operator, the touch screen provides an icon-based script for the operator to follow. A physician's prescription may be networked with the system so that when the subject arrives, any tests and conditions may be preset for the operator.

If the system is used for range of motion, a second screen may include icons such as "Standing", "Seated", and "Reclining." Then, the particular body part needing examination may be selected from a menu or an on-screen human body model. Again, the healthcare professional recommendation or prescription may be directly networked into the system.

A row of buttons at the side of the interface may be suitably included to allow quick navigation between functions. These may include common functions such as "Home", "Forward", "Backward", "Menu", and "Help", for example. Screen space may be conserved by having a single "Tools" icon or "Others" icon which takes the user to a function or state selection 'Menu'.

The "Menu" or "Tools" function may suitably allow the operator to return to where he or she wanted to go if they moved away from a desired location. The "Menu" function may be toggled to "Map" which gives the same information in a flow chart form. This flow chart form may be easier to follow for many operators.

The system may also contain an additional level of password protected administrative functions, such as system tests and maintenance functions. The "Help" screen may contain icons to select tutorials, definitions and explanations. Another icon may be provided which allows a user or operator to choose whether the system is laid out for left-handed entry or right-handed entry, thus customizing the system for right-handed or left-handed users.

Through the use of structured light, the system has all the advantages of a marker-based system, but also includes the advantages of non-invasiveness of a markerless system. Marker-based systems require a highly trained specialist to glue reflective markers to specific locations on the body of a subject. By being markerless, the system eliminates this time-consuming activity.

The structured light pattern used by the system removes range ambiguity by its design. The light is projected using a near-infrared LED and a film pattern. Each spot in this pattern is individually identifiable by the two near-infrared cameras.

Figure 3:
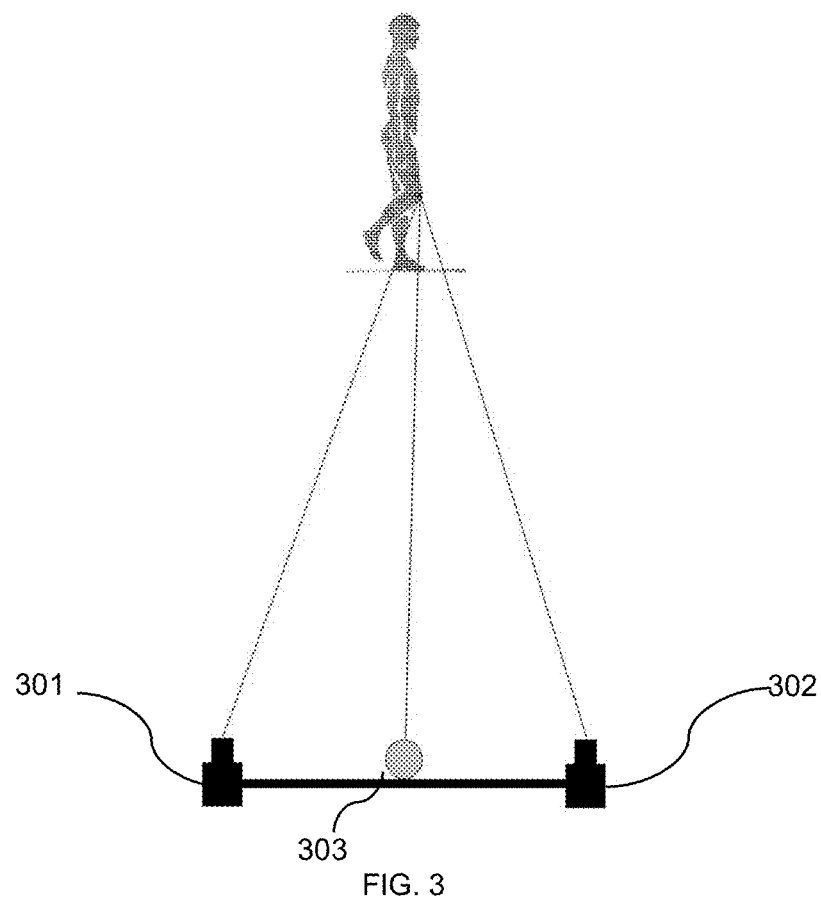
FIG. 3 illustrates a basic geometry of the light source and cameras of a mobility monitoring system.

Reference is made to FIG. 3 which shows the basic geometry used in the supporting analyses. An individual spot is imaged in both the right and the left cameras 301 and 302. The positions of the cameras and the pattern generators are known. Thus, recreation of a three dimensional set of points representative of the subject's body becomes simple geometry. The three dimensional position and velocity of each spot is then used to build a 3D point cloud for the subject.

The point cloud is suitably used to generate a mesh model for the subject. The normals to the facets of the mesh may then be back propagated to the skeletal structure. In addition, an intermediate model generated by fusing the skeletal structure and mesh model by this process is used to generate a shadowing avatar. Further, the color imagery may be used to texture the mesh model and to generate a 3D model that may be rotated during observation to allow all sides of the subject to be viewed such as during walking or attempting to maintain balance. Additionally, a mathematical model, such as a frustrated elliptical cone, may be used to create a model of a body segment. Then, the point cloud positions may be used in a RANSAC algorithm to determine the descriptive parameters and centerline.

Generally, most textiles are somewhat translucent at the near-infrared ("NIR") wavelength range as the dyes are not designed for NIR. Fiber is more transparent in NIR than in the visible wavelength range, and the scattering of light is greatly reduced because the wavelength is longer than in the visible range. Therefore, in using the system, generally any arbitrary clothing may be worn during testing because the movement may still be assessed adequately in this manner. However, it is expected that the system may provide even better results with subjects who are lightly clothed with items that are tight enough to follow the body contour.

Normally, an accurate and robust screening may be done in the subject's street clothes. However, if the results indicate too much margin for error or that the subject has a borderline performance, then further measurement may be done relatively easily using the system described herein by rearranging a subject's attire.

The major components of a mobility monitoring system are depicted in FIG. 4. The three primary cameras are suitably located in the camera bar 402 along with the structured light projection system. The control panel 401 holds a touch sensitive 15-inch 3D capable monitor. In one embodiment, the system has a printer. The control panel and camera bar are held in the correct location with the stand 404.

In another embodiment, a docking station 403 is available off line to charge the system's batteries. Mains power is suitably transferred by transformer action as is done with electric toothbrushes and the like. The base plate may be keyed to ensure it is set into place properly for the transformer to work.

Figure 5:
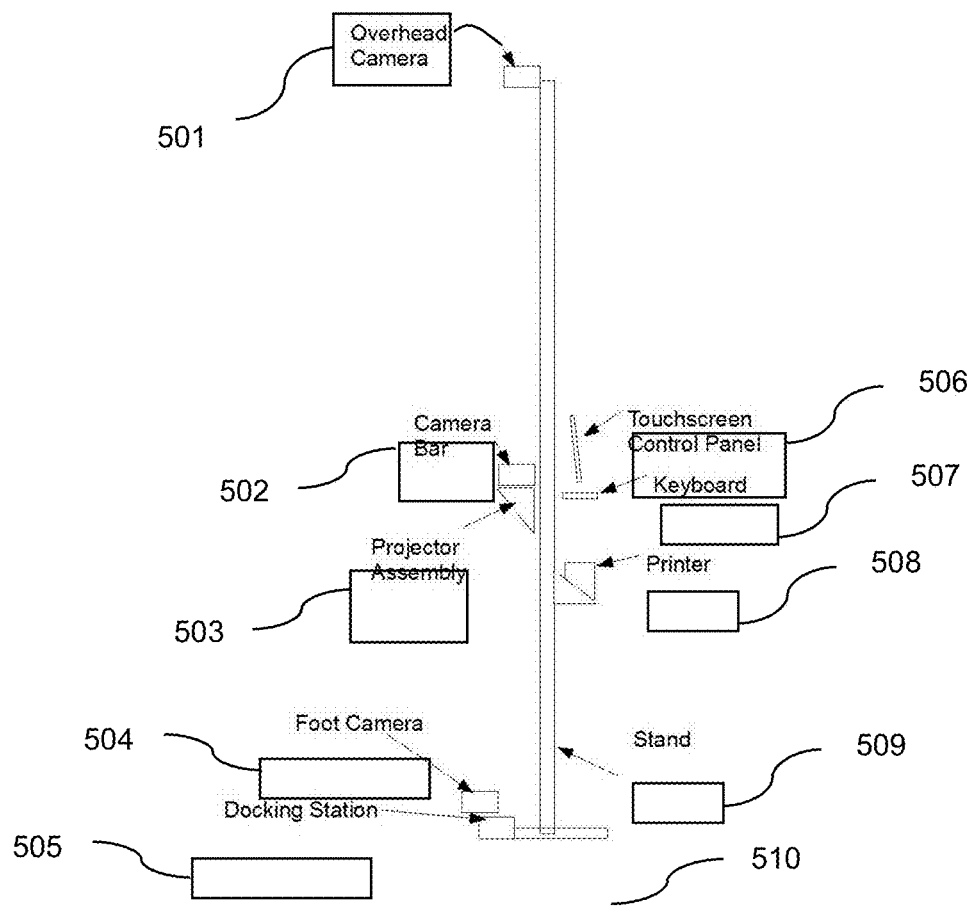
FIG. 5 illustrates main components of another embodiment of a mobility monitoring system.

A foot camera 504, shown in FIG. 5, may be added at foot position and an overhead camera 501 at the overhead position to improve performance for certain conditions. For example, the foot camera 504 improves the tracking of the feet and quantification of foot strike. The overhead camera 501 helps improve the reconstruction of the 3D model of the subject under test. If these enhancements are added, the base area 510 is suitably increased and the diameter of the riser for the top camera is suitably minimized.

Figure 19:
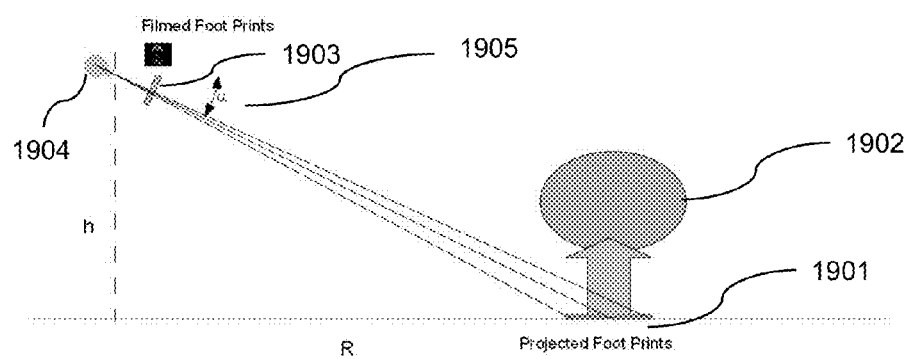
FIG. 19 depicts filmed foot prints and projected foot prints.

As shown in FIG. 19, the system may have pattern projectors 1903 (also 203) and 1904 (also 204) to show where the subject has his or her location at the start, and then the system shows the subject when to move and when to turn around. These directions may be augmented with verbal instructions to allow use by the visually impaired.

For gait analysis, the system may show a pair of green footprints 1902 on the ground 1901 at the location where the subject is to start moving. For example, the subject may be instructed to walk straight toward the green arrow, and to turn when he or she sees the green arrow replaced with a red turn-around symbol. The green arrow and turn-around symbol are projected ahead of where the subject may turn around to minimize affecting the movement of the subject. Either the operator may deliver the instructions or the system may judge a subject's responses and give appropriate instructions.

Figure 6:
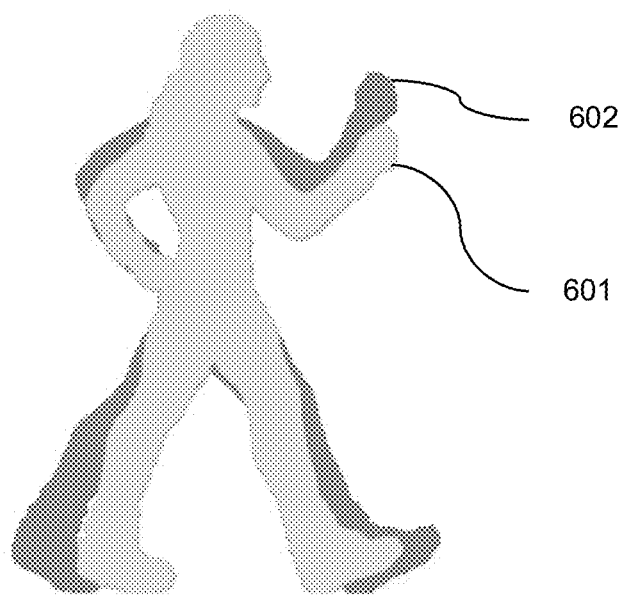
FIG. 6 illustrates one embodiment of shadow avatars used for a range of motions of a subject assessed by a mobility monitoring system.

After a test is complete, the subject may be shown their gait as it compares to a normalized plot or to their prior test results. The subject may appear in rendered 3D from the depth data obtained from the near-infrared cameras. A slider on the touch pattern may suitably allow the operator to control the transparency of a subject 601 and observe the shadow avatar 602 behind. (See, FIG. 6). In a more transparent mode, the subject may be able to see a gray 'ghost' figure representation of the subject, representing the normal range for their age. If it is a Returning Person, his or her historical data may be suitably displayed as green if significant progress or improvement in motor skills has been made, yellow if nominal improvement in motor skills has occurred, and red if regression of motor skills has occurred.

A similar process may be done using the mobility monitoring system with a variety of other performance assessments, such as rising from a chair, balance, bending down, reaching, and turning in place. Also, other range of motion conditions may be assessed such as neck and arm movement, hand flexure, and spine bending.

The database of the system may suitably contain a full range of anthropometric, biomechanic and biodynamic data.

Suitably, the system may be broken down to be packed in a case for portability. Other manifestations of the system may include a fixed station mounting, wall mounting, etc.

A simplified version of the system using only the NIR camera and structured light projector may be suitably used to monitor activities of daily living at a subject's home, and may be used to provide an alarm in the case of a subject falling down and not being able to recover. This feature is particularly important for maintaining independence in the elderly.

A further embodiment of the system may be used to provide detailed metrics of wounds and skin ulcers. A degree of assessment of wounds may be done by simply operating the system in a close-up mode. Because of shadowing, this method may suitably contain an on-board light source, such as a white-LED, for color. In this application, the stereo cameras may be moved adjacent to the color camera and light sources. The system may be mounted on a hand held probe to image the skin. By choosing two wavelengths to be multiplexed for the structured light, analysis of the surface constituents may be performed.

Figure 7:
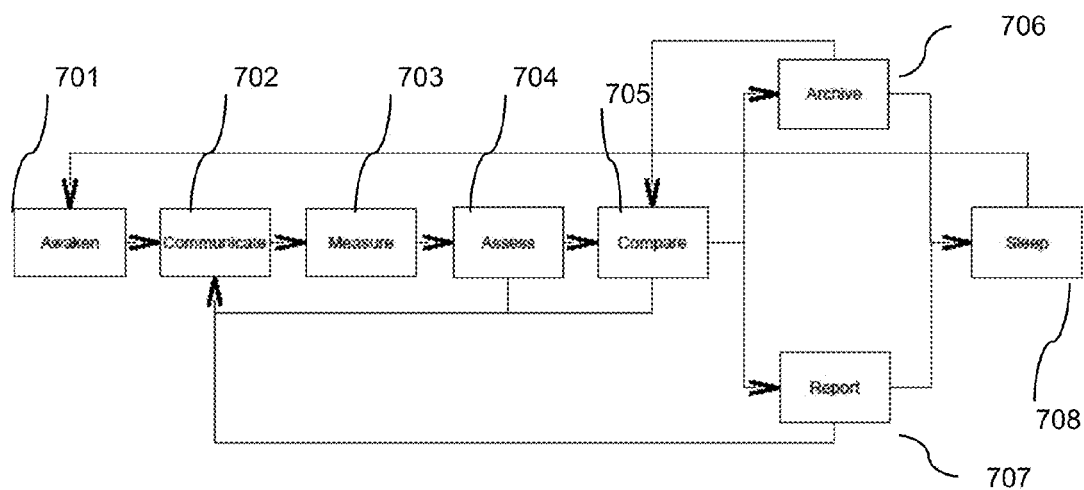
FIG. 7 is flow diagram of a mobility monitoring system.

A top level functional flow of the system is shown in FIG. 7. The functional flow diagrams may serve multiple purposes in refining or clarifying the design of the system.

When the operator moves the assembly away from the dock (charger), the system initiates an awaken function 701, which brings the system into full operation. Upon completing this function, the system via a Communicate function 702 communicates with the operator to inform him or her that it is ready to perform its functions. This may be done with audio using a speech synthesizer (or other means), visually by a light, or on a display screen. Upon initiation of the test, the system via the Communication function 702 communicates with the subject under test to tell him or her where to stand, what activity is expected, when to start activities, and when to change mode. Additional data may be communicated to the operator to show health and status of the system or other information necessary to the operation.

At a Measure function 703, the system measures the instructed activities; then, at an Assess function 704, the system assesses the performance. At a Compare function 705, the system compares the results with the subject's previous activities which are the same as those under scrutiny, and/or with the normal expectations of a subject having that tested subject's profile. This information is retrieved from an archive 706. Data from the Measure function 703 and comparison from the compare function 705 are saved in the archive 706, and at a Report function 707, the results are reported to the operator via, e.g., a display screen.

Upon being re-docked, the system may return to a sleep mode via Sleep function 708. After a test, if no further instructions are given to the system for a preset period of time, the system may go to sleep without being docked. The latter allows extension of battery operation.

Figure 8:
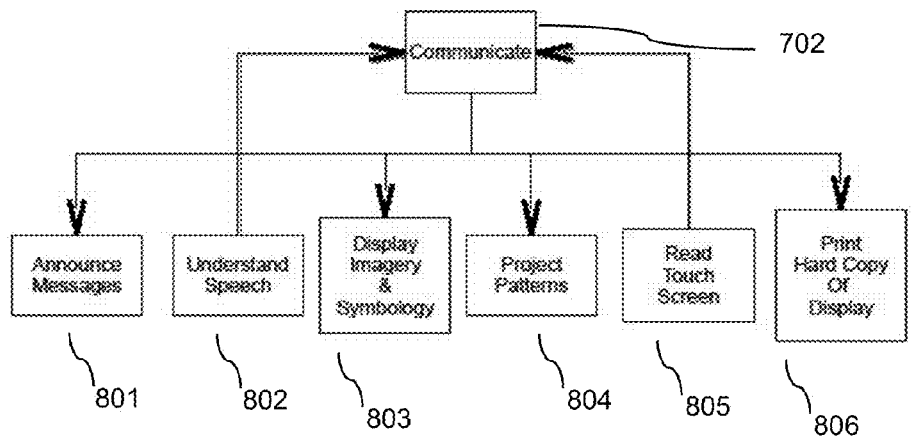
FIG. 8 is a flow diagram of the communication function of a mobility monitoring system.

The Communicate function 702 is broken down to the next level in FIG. 8. As the system goes through its process of giving instructions to the operator, aural messages are generated using an Announce Messages sub-function 801 or a Display Imagery & Symbology sub-function 803. Response from the operator is accepted with annunciation to an Understand Speech sub-function 802 or tactilely accepted with a Read Touch Screen sub-function 805. The subject is instructed via the Announce Messages 801 and a Project Patterns sub-function 804. The operator may accept messages from scripts displayed by the system and annunciate them directly to the subject, if need be. The subject's responses to instructions may be entered directly via the Understand Speech 802 if the subject is wearing or near a microphone or by way of operator inputs verbally via the Understand Speech 802 or intervention via the Read Touch Screen sub-function 805. Such responses would be in answer to the systems inquiries, for example, "Are you Jane Smith?" for verification of being the correct subject. The Announce Messages and Understand Speech sub-functions, 801 and 802, respectively, may use open source software. However, the use of speech as operator/subject interface is suitably a feature of the system. A Print Hard Copy of Display sub-function 806 uses a mini photoprinter to produce a replication of the display for the subject and others who may require it.

The Project Patterns sub-function 804 generates patterns for system metrics and shows patterns to provide instructions to the subject. These may include items such as footprints showing where to stand, arrows to indicate direction to walk, markers where to reach and arrows showing when to turn. Each of these patterns may have its own projector, or a rotational system similar to a slide projector may be used. In situations where the projector points in the same direction, the projector may be used like a slide changer to change the pattern for a single projector.

The system metrics patterns are the structured light pattern and a line marking the path the subject is expected to follow. The latter would be invisible to the subject. Thus, any wandering from an expected line may be measured. Further, this line may be used to calculate the head angle, to reinforce measurements of a resolver.

Figure 9:
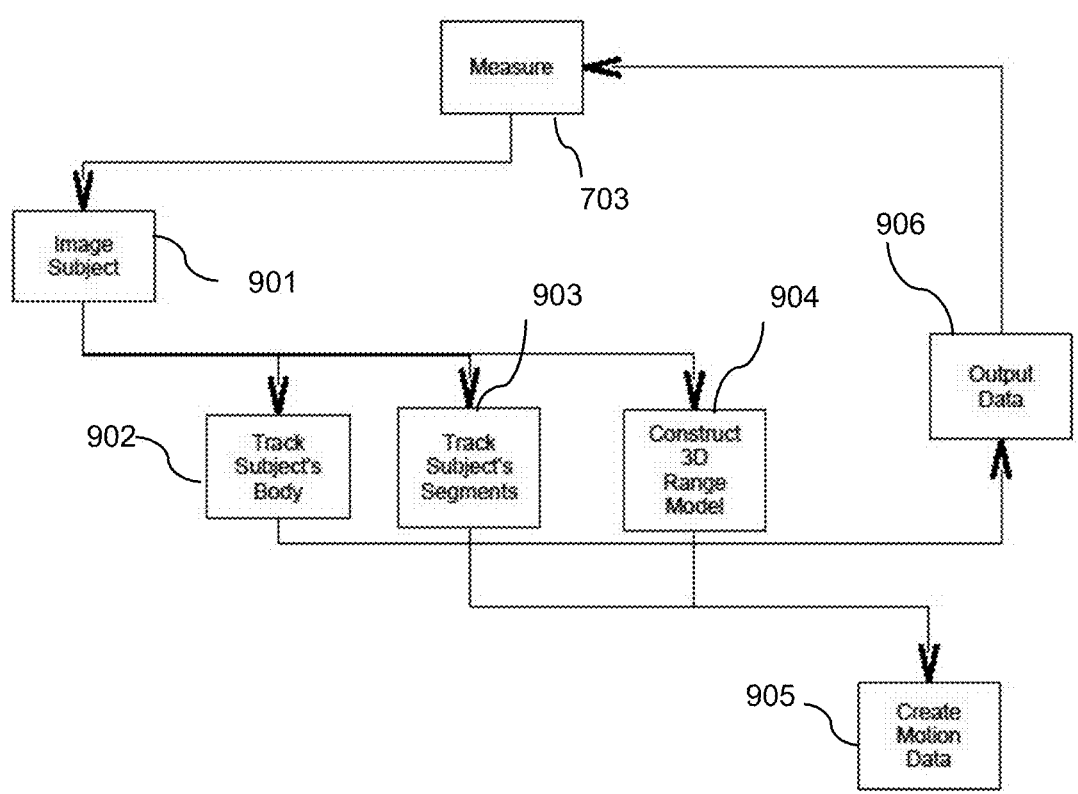
FIG. 9 is a flow diagram of the measure function of a mobility monitoring system.

Sub-functions of the Measure function 703 are shown in FIG. 9. An Image Subject sub-function 901 acquires motion images of the subject at a constant scale. The baseline system includes a pair of stereo cameras on a long baseline and a color camera at the center. This function may be further enhanced by placing a camera at ground level which images the movement of feet with minimal perspective distortion. Additionally, a camera may be placed at a high point (for example, near the ceiling) to look down on the subject to get a more accurate measurement of the convex hull produced by the body. Each of the cameras may use System on Chip (SoC) technology to render them highly intelligent. Conventional cameras may easily be used with a smart enough and fast enough central computer. However, using SoC technology may result in a much lower system cost.

A Track Subject's Body sub-function 902 processes the output color imagery to maintain the subject at the center of the screen. As this tracking function covers a rather mundane object to track, the implementation may be rather simple. Motion estimation engines used for image compression may be more than adequate to detect and quantify the motion. This collected image data may feed into either a simple filter or a predictive filter to determine the error needed to be minimized by the control system. The filter utilized in the control function to maintain center may be a proportional integrator differentiator ("PID"). By maintaining constant scale, the tracking is greatly simplified.

The stereo cameras image the subject illuminated by the structured light that is produced by the Project Patterns sub-function 804 in the near-infrared region. Although the visible region may be used, the NIR projected patterns are less objectionable to the subject under test and are less affected by clothing patterns as previously noted because many items are transparent or semi-transparent to NIR.

The local variations of the projected pattern, which in this implementation is spots, are used by a Track Subject's Segments function 903 to obtain a 3D optical flow image of numerical values for range and local three-axes velocities at each pixel location. The same motion estimation filters used by the track body function may be suitably used to track the individual spots and to help determine the local velocity. The ensemble of spots may be tracked using a particle filter, a nonlinear extension of a Kalman filter designed to track sets of points.

The optical flow data is processed to obtain the "hinge points" for the motion. This optical flow data is then mapped against a human body model to obtain joint motion in a Create Motion Data sub-function 905.

A Construct 3D Range Model sub-function 904 uses the stereogrammatical information from the two cameras. The designed structured light pattern creates a spot at an angle representing every 2.5 cm on a flat target normal to the projector. There may be one or more additional projectors, which are then mounted near the cameras. Each projector also provides angularly calibrated positions relative to the cameras, effectively allowing trinocular vision. Further, the spatial information from the color camera may generate an angular mask for the subject's location. If the overhead camera is used, these projected spots become a contour map representation of the convex hull of the body. All of the independent measures may be fused together to arrive at the most accurate representation of the point cloud at the subject.

The output of the Track Subject's Segments sub-function 903 and the Construct 3D Range Model sub-function 904 may be fused in the Create Motion Data sub-function 905 to generate data in the expected form, such as joint angles and velocities. A human body model places constraints upon the calculations.

Figure 10:
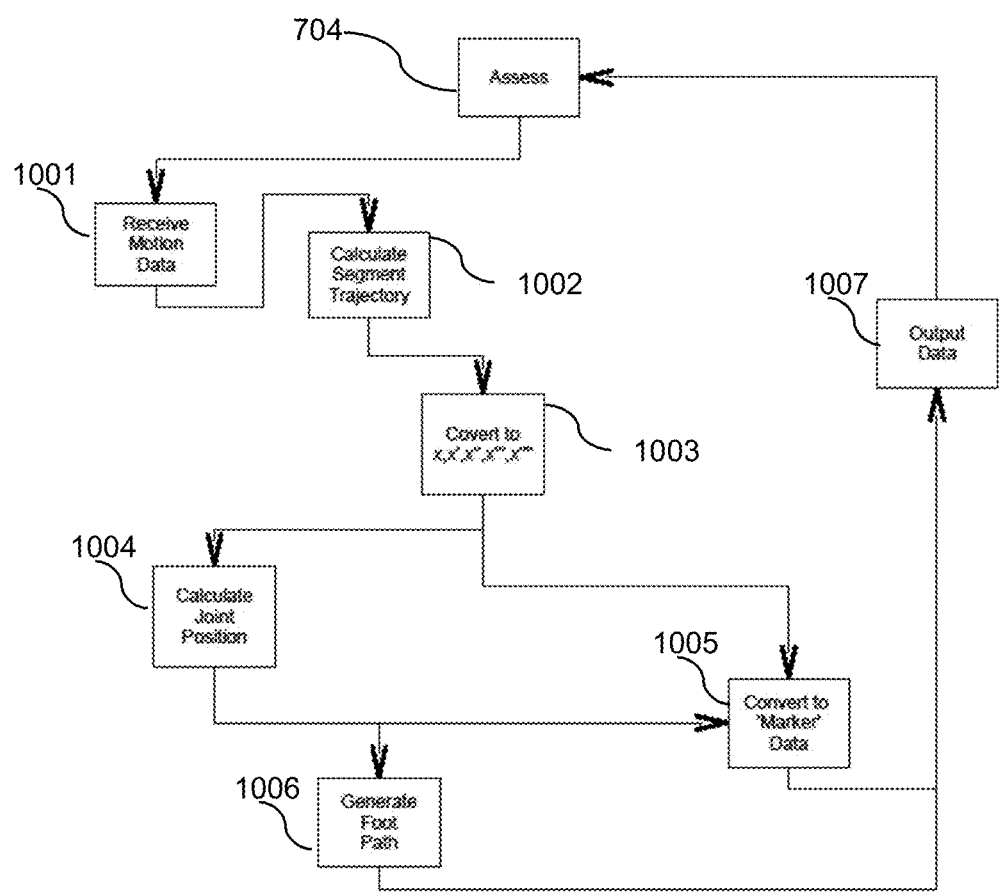
FIG. 10 is an flow diagram of the assess function of a mobility monitoring system.

FIG. 10 depicts the functional flow of the Assess function 704. The mobility monitoring system receives motion data 1001 from the Measure function 703. The segment trajectory is calculated at step 1002 by determination of the motion of the centroid of the object. This is in the form of position of the spot in all three Cartesian axes (x, y, z) from the spot centroids. Further, the motion estimation gives the velocities along all three axes (x', y', z'). This information is processed to derive the acceleration (x", y", z"), jerk (x'", y'", z'") and snap (x"", y"", z""). (A convert sub-fraction 1003). The latter is the highest order term normally found in human motion. Although, the presence of higher order terms are able to be assessed in robust statistical processing as a factor to throw out an outlier. Further, it should be noted that the third derivative of position is usually assumed at or near zero. Thus, significant values for that and higher derivatives are treated as suspect in the processing.

These data are used to extract the joint positions (at a Calculate Joint Position function 1004) with blind source separation methods. The system may implement independent component analysis or principle component analysis. From the Convert function 1003, it is possible to proceed to a Convert to Marker Data function 1005, and then to an Output Data function 1007, before returning to the Assess function 704. From the Calculate Joint Position function 1003, the system may proceed to the Convert to Marker Data function 1005. Otherwise, the system may proceed to a Generate Foot Path function 1006 and then proceed to the Output Data function 1007, before returning to the Assess function 704.

Figure 11:
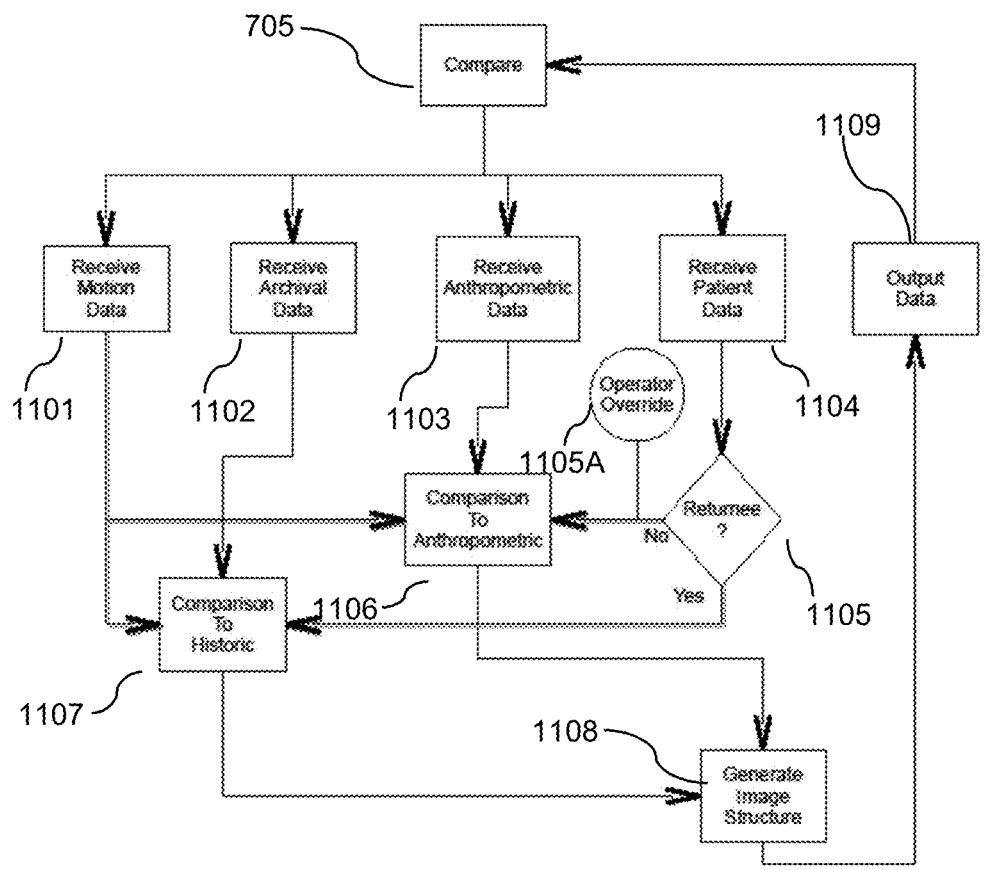
FIG. 11 is a flow diagram of the compare function of a mobility monitoring system.
Figure 12:
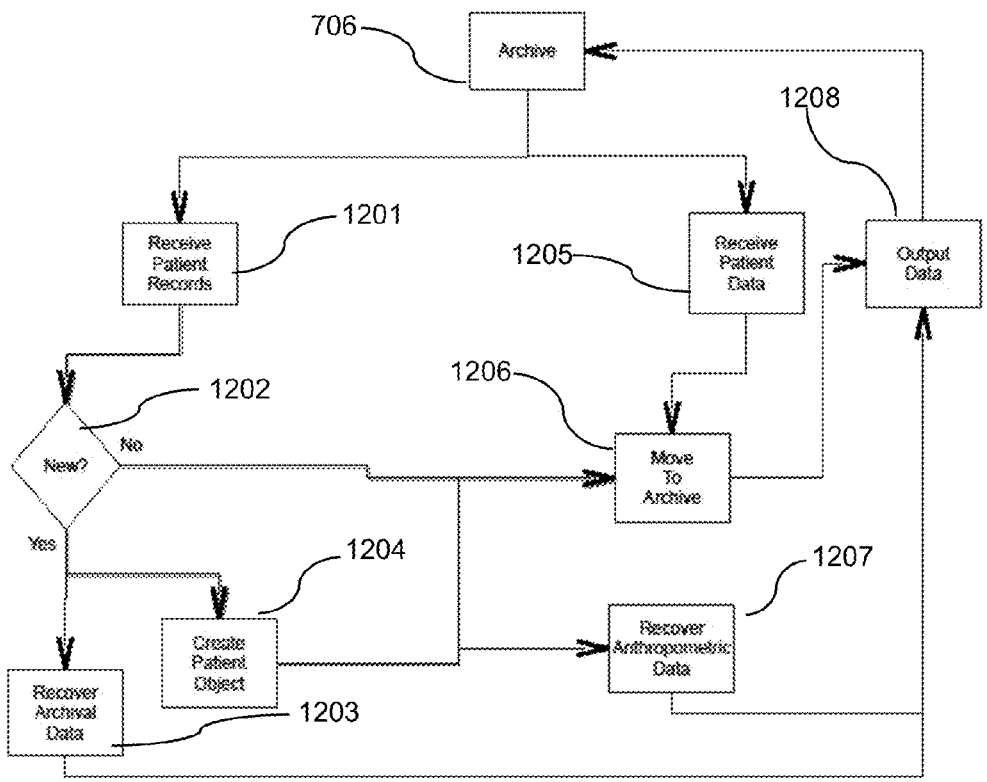
FIG. 12 is a flow diagram of the archive function of a mobility monitoring system.
Figure 13:
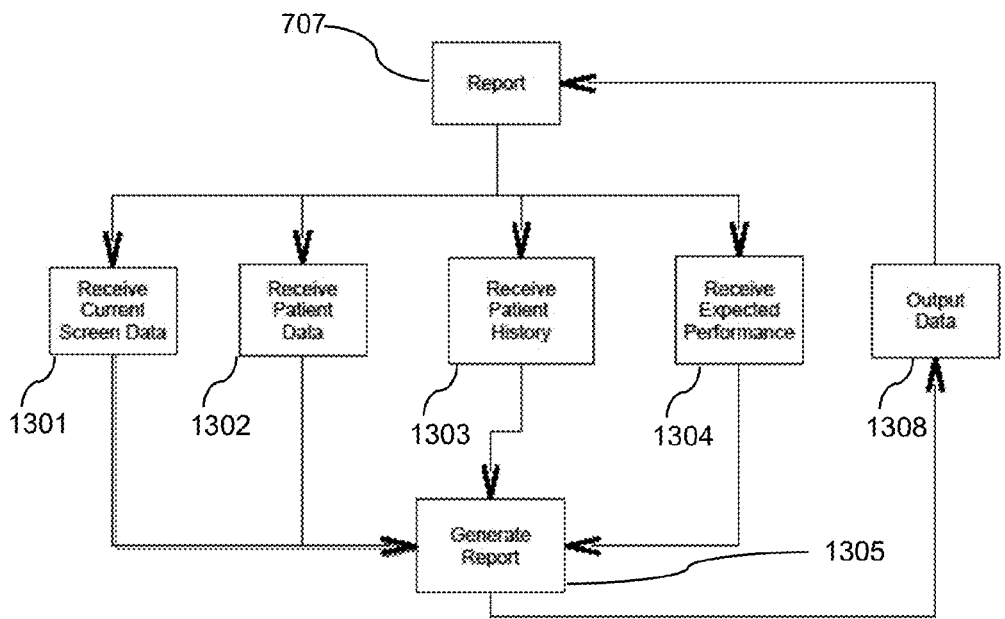
FIG. 13 is a flow diagram of the report function of a mobility monitoring system.

FIG. 11 shows the Compare 705 functional flow, FIG. 12 shows the Assess 704 functional flow, and FIG. 13 shows the Report 707 functional flow.

The baseline system includes three primary elements, namely the stand 404, the control panel 401, and the camera bar 402 as shown in FIG. 4. Functionally, the stand holds the other elements in place and may have batteries stored therein for off-main or system powering operations. Located behind the control panel in FIG. 4 is a printer to provide reports to the operator, subject under test and other interested parties. A secondary element is the docking station 403 which contains a charger and connection to the mains. Also, direct connection from the base to the mains is an option. Further elements for the expanded version of the mobility monitoring system may include the overhead camera 501 mounted on a vertical structure above the camera bar for overhead measurements and the foot camera 504 on the base of the stand to measure the positions and velocities of the feet. Further sensors may be added to enhance the full characterization of the subject. Among these are suitably to add a camera or exploit information from one or more of the existing cameras to take imaging photophlethysmographic data.

Further, the system may be expanded to process data from other sensors such as foot pressure sensors, electromyographs ("EMG"), accelerometers and other sensors along with other systems. The latter suitably allow simultaneous tracking of multiple views of the same subject. When having a synchronization signal and allocating time slots, the different systems would not interfere with each other because each system has its shutter enabled for a small amount of time.

The stand 404 contains the projector for the NIR line on the floor to give "on the fly" position calibration to the NIR cameras. The projector also projects the starting position for the subject, the direction of travel, turnaround time, etc. for gait assessment. For ADL, drawers and doors may be projected for the subject to "open" to gauge minimum flexibility. The projector may project a pattern for locating a "coin" to be picked up.

In another test, the location of the phone may be measured and the subject's interaction with the phone quantified. New projection patterns for other functions may be readily added to the system as needed. The projectors may each contain one slide or a slide changing mechanization. Objects for interaction may also be real as opposed to the virtual items described above.

Figure 14:
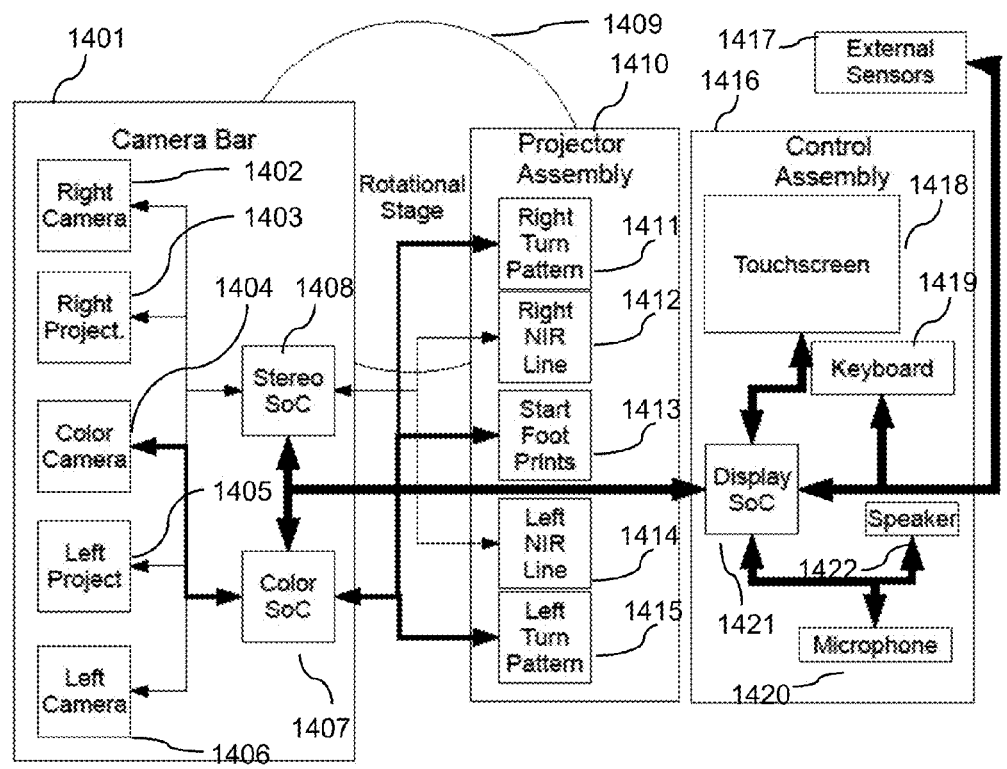
FIG. 14 is a block diagram of one embodiment of a mobility monitoring system.

One embodiment of a mobility monitoring system is shown in FIG. 14. The cameras and their associated system-on-chip ("SoC") technology are tightly coupled and may be considered as a single smart camera. The Color Camera 205 and its associated SoC technology process the color imagery, and the two stereo cameras and their associated SoC technology process the stereo imagery. Command and control of the system is handled by a Display SoC technology. The system accepts commands from the operator and sends instructions to the operator and the subject under test.

This implementation assumes that the SoC technology contains as a minimum, camera interfaces, display/audio interfaces, general purpose processing unit(s), a graphical processing unit, and a digital signal processor. These subelements may be implemented in separate hardware, but the objective of the design is to minimize cost and hardware complexity. The particular embodiment uses a Texas Instrument OMAP4460. However, other advanced processors from Texas Instruments and other vendors may be used. In particular, the OMAP5430 is contemplated because it has more capability.

The Project Patterns sub-function 804 shows patterns to provide metrology to the system and instructions to the subject. The latter includes items such as footprints showing where to stand, arrows to indicate direction to walk, markers where to reach and arrows showing when to turn. Each pattern suitably has its own projector, or a rotational system similar to a slide projector may be used. If the projector points in a single direction, it may be a dedicated projector. If multiple patterns have to be shown in the same direction, the projector may be a 'slide changer'. The order in which the slides have to be shown may affect the requirements for the mechanism. For example, if there are two patterns, the mechanism may slide back and forth into or out of the path from the light source. This changing may be either mechanical or optical. The latter may be achieved by changing the color of the source to match the projected object.

In addition, there are two patterns used for the metrology performed by the mobile monitoring system. These are the structured light pattern, in this particular case, spots, and a line to show the straight path of travel expected of the subject. The function performed by the line may be another pattern such as a series of particularly shaped markers.

Figure 15:
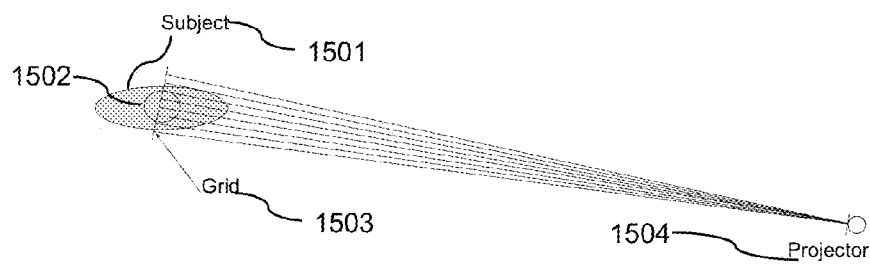
FIG. 15 is a diagram illustrating how a structured light pattern projector projects a grid on a subject.

The projection method using the structured light is a complex of the patterns. The structured light pattern projector 1504 (also 204) adjusts the distance from the point source to the film to give an angle such that it projects a grid 1503 of spots (spaced at, for example, one inch or 2.54 cm centers) at the subject's centroid 1502, as shown in FIG. 15.

The Project Patterns sub-function 804 uses structured light to determine positions in three-dimensions over a calibrated scale. For gait and balance assessment, this particular embodiment places one spot every inch covering a range of over 9 feet. The NIR Camera is designed to have five pixels per inch. This configuration gives an image height of 540 pixels.

In one embodiment, the camera centerline is 36 inches above ground. This configuration places 12 inches of pattern upon the floor in front of the design centerline. This gives a height of 84 inches above the floor being sensed at the design distance from the camera. In another aspect, the structured array is 156 V by 88 H spots which is imaged with 624H× 312V pixels. The required horizontal spots are only 78, but the 10 additional spots allow for slight misalignments. For walking, the horizontal resolution may be reduced to 200 pixels thus allowing for an increased frame rate.

The spot pattern is a reticle of four levels of brightness. The brightest spots mark three inch increments between the limits along each axis. The one foot marks are a five spot pattern roughly as a '+'. The six inch marks are three spot '–' along the grid axis. Specifically, the horizontal grid includes '–' and the vertical grid includes '|'. The other three levels are used to produce a locally unique pattern at the individual locations. An example taken from a proposed upper left hand corner of the pattern is shown in Table 1.

are effectively transparent to it. A wavelength of 0.85 μm may be suitably used. This wavelength is sufficiently long enough to see the desired effect and sufficiently short as to have a high response in the camera.

Structured light is based on a number of infrared light emitting diodes arranged in an integrating sphere 1601. The limiting stop forms the exit pupil which limits the light able to exit to the angle formed by the length of tube and diameter of the tube. The exit pupil of the sphere and spacing from it to a pinhole 1604 ensures that virtually all of the light from the diodes goes into the pattern projection.

Through the use of the projected structured light pattern, the mobility monitoring system has the advantages of a marker based system with the non-invasiveness of a markerless system. By using coded points, the structured pattern removes range ambiguity. Each spot is individually identifiable by the two near-infrared cameras. The positions of the cameras and the pattern generator are known. In addition, the angles of the spots are known from the position of the slide with respect to the point source. Thus, recreation of a three dimensional mesh representation of the subject under observation becomes simple geometry of the structured light source and cameras.

The selected method does not require focusing. "Zooming", if desired, is performed by adjusting the distance between the pinhole 1604 and the light pattern 1605 or 1606. In this implementation, the position is determined by counting the teeth in the drive belt from the forward seated position. Other resolving methods are possible.

The pattern may take advantage of the high signal to noise ratio and use four levels at the landmarks in a sparse matrix. As implemented, the blurring due to the finite aperture of the source, camera, etc. makes the points nominally gaussian. The maximum level (4) is set to be imaged at about 90% of camera saturation. The light intensity of level 3 is ¾ level 4, etc. The pattern is generated with a 156 by 88 array of intensities ranging from levels 1 through 4. These intensities are in a pseudorandom pattern defining each location with a code of the surrounding spots. The spots are of uniform maximum brightness, but of proportional cross sectional areas. This limits errors generated by the pattern of material being worn by the test subject. The spots are detected using a filter matched to the spatial diameter of the spots using a gaussian matched filter.

TABLE 1

| 4 | 4 | 3 | 4 | 3 | 3 | 4 | 3 | 1 | 4 | 1 | 4 | 4 | 4 | 2 | 4 |
|---|---|---|---|---|---|---|---|---|---|---|---|---|---|---|---|
| 4 | 3 | 3 | 2 | 2 | 1 | 2 | 2 | 1 | 2 | 2 | 3 | 4 | 3 | 3 | 2 |
| 3 | 1 | 3 | 2 | 1 | 2 | 2 | 1 | 2 | 1 | 3 | 3 | 1 | 1 | 1 | 3 |
| 4 | 3 | 2 | 4 | 2 | 1 | 4 | 3 | 1 | 4 | 2 | 3 | 4 | 1 | 2 | 4 |
| 3 | 2 | 2 | 2 | 2 | 2 | 3 | 2 | 2 | 1 | 1 | 1 | 1 | 2 | 2 | 3 |
| 1 | 1 | 3 | 3 | 3 | 3 | 1 | 3 | 1 | 1 | 1 | 2 | 2 | 3 | 3 | 1 |
| 4 | 2 | 2 | 4 | 1 | 3 | 4 | 2 | 2 | 4 | 3 | 3 | 4 | 2 | 3 | 4 |
| 3 | 1 | 2 | 2 | 3 | 3 | 3 | 2 | 1 | 1 | 2 | 2 | 2 | 3 | 3 | 2 |
| 4 | 2 | 1 | 2 | 2 | 3 | 2 | 3 | 3 | 3 | 2 | 3 | 4 | 3 | 1 | 3 |
| 4 | 4 | 1 | 4 | 2 | 2 | 4 | 1 | 3 | 4 | 3 | 4 | 4 | 4 | 2 | 4 |
| 4 | 3 | 1 | 2 | 1 | 3 | 2 | 1 | 2 | 2 | 2 | 3 | 4 | 1 | 2 | 1 |
| 1 | 1 | 1 | 1 | 1 | 3 | 1 | 2 | 2 | 2 | 1 | 2 | 1 | 1 | 1 | 1 |
| 4 | 1 | 1 | 4 | 1 | 1 | 4 | 2 | 2 | 4 | 3 | 1 | 4 | 2 | 3 | 2 |

An alternative embodiment has an array of 156×88 spots of pseudorandom intensity values representing one through four.

Figure 16:
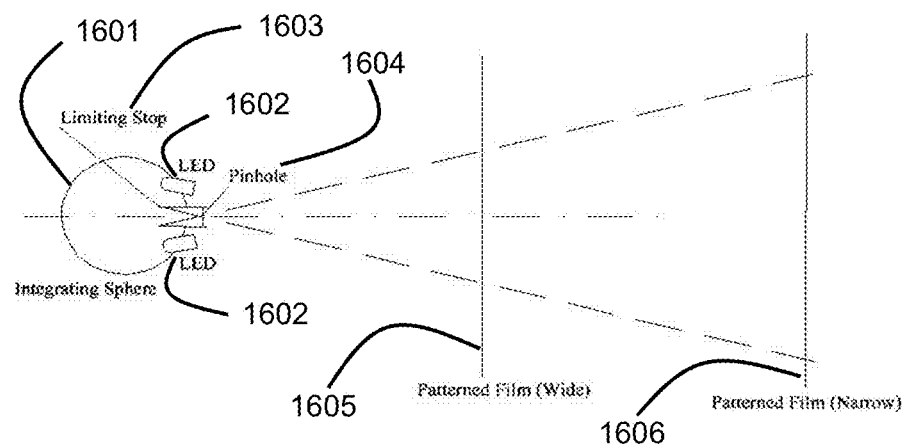
FIG. 16 is a diagram illustrating a projection pattern of a structured light projector in the wide and narrow positions.

Structured light allows marker accuracy without the complexity of intrusive markers or errors from misplaced markers. As noted, infrared light is chosen because most materials One of the projectors from the Project Patterns sub-function 804 is depicted in FIG. 16. This is a structured light projector. The source for structured light is based on a set of infrared light emitting diodes 1602 ("LED") in the integrating sphere 1601. A limiting stop 1603 is the exit pupil of the sphere 1601 and spacing to the pinhole 1604 ensures that virtually all of the light from the diodes goes into the patterned film 1605 or 1606 for projection.

As noted, selected method does not require focusing, and "zooming", if desired, is a matter of adjusting the distance between the pinhole and the 'slide'. Other embodiments may use a laser illumination of a diffractive optical element or a microprojector.

There are suitably sixteen LEDs in the light source. The current design uses Huey Jann HIRPB8-1x. At full power, the LEDs may provide approximately 175% of that amount of light required at the planned maximum range.

Figure 17:
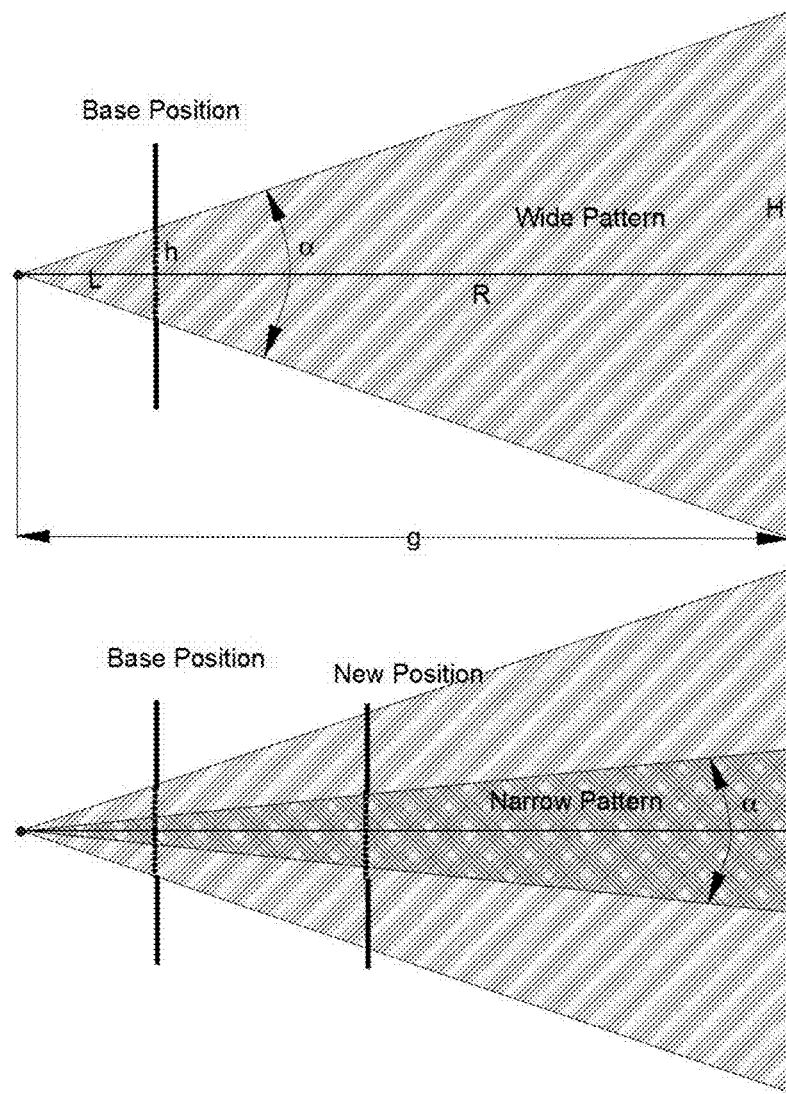
FIG. 17 is a diagram illustrating a zoom process of a projected structured pattern.

If one considers that when full, the patterned film is the projected image seen in FIG. 17, then one may observe that the film pattern and the projected pattern are similar triangles. That is, the half image height ("h") divided by the distance from the light source ("L") is proportional to the half-height of the projected image ("H") divided by the distance to the screen ("R"). The arctangent half height of the film ("h") divided by the distance to the pinhole is half the arctangent of the projected field of view.

$$\frac{h}{L} = \frac{H}{R} \tag{1}$$

$$\frac{\alpha}{2} = \arctan\left(\frac{h}{L}\right) \tag{2}$$

$$H = R\arctan\left(\frac{\alpha}{2}\right) \tag{3}$$

The use of the integrating sphere and pinhole suitably creates a point source. In this particular design, in addition to the smaller source, the more monochromatic light from the infrared LEDs gives better performance than possible with an incandescent light. Also, there is less heat produced.

Settles (2001) gives the minimum useful light source diameter, the onset of diffraction fringing in the projection, as:

$$D_{min} = 1.33\sqrt{\frac{\lambda \cdot R(R-g)}{g}} \tag{4}$$

where
  $\lambda$ is the wavelength
  R is the distance from the source to the target
  g is the distance from the slide to the target
In the terms associated with FIG. 17.

$$g = R - L \tag{5}$$

The equation then becomes $$D_{min} = 1.33\sqrt{\frac{\lambda \cdot R \cdot L}{R-L}} \tag{6}$$

Using these terms, Settles (2001) gives the minimum resolvable spot as:

$$\delta_{min} = 1.33\sqrt{\frac{\lambda \cdot (R-L)L}{R}} \tag{7}$$

Relating these two equations (17) & (18) gives:

$$\frac{\delta_{min}}{D_{min}} = \frac{R-L}{R} \tag{8}$$

Conventional wisdom uses the Rayleigh criteria of $$\varepsilon = 1.22\frac{\lambda}{D} \tag{9}$$

The baseline system described herein calls for the target area height to be $$H = 4 \text{ ft} = 1.220 \text{ m} \tag{10}$$

There are two distances of interest for the system. The first is the distance straight ahead or the minimum distance. The second is at the nominal maximum distance. This is the diagonal distance to the subject when they are at their maximum excursion during the walk. The system optical range is based upon a path length of 3.1 meters on either side of the camera. With the distance from the camera to the path being $$R_{camera} = 1.829 \text{ m} = 6 \text{ ft} \tag{11}$$

The maximum range is $$\begin{aligned} R_{max} &= \sqrt{R_{camera}^2 + \left(\frac{L_{path}}{2}\right)^2} \\ &= \sqrt{1.829^2 + 3.1^2} \\ &= 3.6 \text{ m} \end{aligned} \tag{12}$$

At the starting position, the distance from the slide to the screen is $$g = R - L = 6 \text{ ft} = 1.829 \text{ m} \tag{13}$$

For 35 mm film, the film half height is h=0.012 m and for 120 films, the masked half height is h=0.027 m (actual full width negative size is 54 mm).

This gives the relationship where $$\begin{aligned} \frac{\alpha}{2} &= \tan^{-1}\frac{H}{R} \\ &= \tan^{-1}\frac{1.220}{1.829} \\ &= 33.7° \\ &= 0.588 \text{ rad} \end{aligned} \tag{14}$$

and $$\begin{aligned} \frac{\alpha}{2} &= \tan^{-1}\frac{H}{R} \\ &= \tan^{-1}\frac{1.220}{3.6} \\ &= 18.72° \\ &= 0.327 \text{ rad} \end{aligned} \tag{15}$$

Solving Equation (1) for L $$L = \frac{hR}{H} \tag{16}$$

-continued $$g = R - L = R - \frac{hR}{H} = R\left(1 - \frac{h}{H}\right) \quad (17)$$

$$R = \frac{g}{1 - \frac{h}{H}} \quad (18)$$

For 35 mm film at minimum distance, the pinhole to the subject is $$R = \frac{1.829}{1 - \frac{0.012}{1.220}} = 1.847 \text{ m} \quad (19)$$

$$L = g - R = 1.847 - 1.829 = 0.018 \text{ m} \quad (20)$$

The design maximum distance from the pinhole to the subject is $$R = \frac{3.600}{1 - \frac{0.012}{1.220}} = 3.636 \text{ m} \quad (21)$$

$$L = S - R = 3.636 - 3.600 = 0.036 \text{ m} \quad (22)$$

Increasing the film size will increase the number of available spots. The increase is by the square root of the size. For example, four times the film size will double the available spots. Likewise, doubling the film size will increase the spots by 41%. Increasing the film to 46 mm will give enough distance for resolving 96 black spaces equal to the 96 white spots. This would require a pinhole to film distance of 36 mm.

For 120 film, $$R = \frac{1.829}{1 - \frac{0.027}{1.220}} = 1.870 \text{ m} \quad (23)$$

$$L = S - R = 1.872 - 1.829 = 0.043 \text{ m} \quad (24)$$

The maximum distance is $$R = \frac{3.600}{1 - \frac{0.027}{1.220}} = 3.681 \text{ m} \quad (25)$$

$$L = S - R = 3.681 - 3.600 = 0.081 \text{ m} \quad (26)$$

For a fixed slide, the required travel of the point source is 0.073−0.043=0.030 m.

Thus, Equation (10) becomes $$\delta_{min} = 1.33\sqrt{\frac{\lambda \cdot (R-L)L}{R}} \quad (27)$$

$$= 1.33\sqrt{\frac{0.855 \times 10^{-6}(1.870 - 0.043)0.043}{1.870}}$$

$$= 0.252 \text{ mm}$$

at minimum range. This gives the maximum number of spots resolvable over a 120 slide as 214.

$$\delta_{min} = 1.33\sqrt{\frac{\lambda \cdot (R-L)L}{R}} \quad (28)$$

$$= 1.33\sqrt{\frac{0.855 \times 10^{-6}(3.681 - 0.081)0.081}{3.681}}$$

$$= 0.348 \text{ m}$$

at maximum range. This gives 156 spots over the 120 slide

The pattern may be shot from a flat panel display on a 120 camera using orthographic film. Among additional features of the Project Patterns 804 is position guidance for the system. The system projects an infrared line running from the start and finish of the walking path. This location is processed separately, and line information is converted to a range from the current camera bar pointing angle. This line is spatially filtered using a line filter from the same stereo camera information providing the spots. This filter may be based upon a Laplacian calculated for the line size. The output of the filter is directed into a separate processing thread for determination of the range to the target for zoom purposes. It also provides the scene vector representation of the path for determination of foot angle with the floor.

At the same time, a 156 by 88 dot matrix may be projected straight ahead relative to the two stereo cameras, there may be an infrared line projected between the endpoints of the walk pattern. This walk pattern is straight ahead relative to the system.

Figure 18:
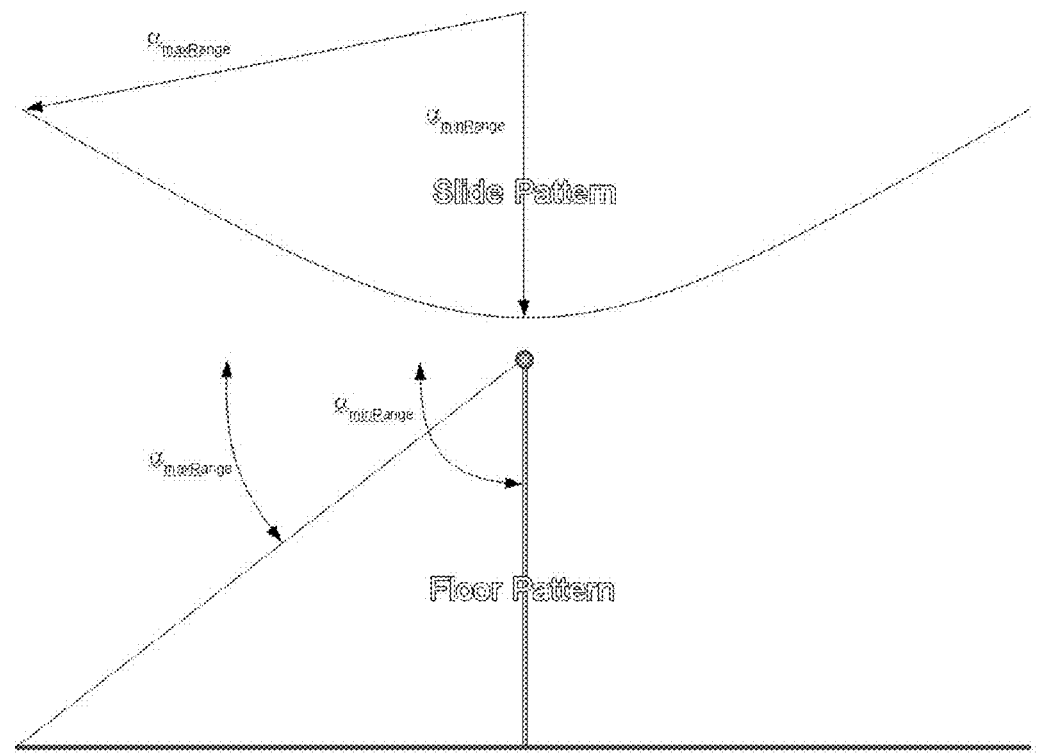
FIG. 18 depicts a slide pattern versus a floor pattern.

If the projected line pattern is above the centerline of the film, then it is a secant curve based upon the height and range is such that the pattern on the floor is a straight line (see, FIG. 18).

For that reason, it may be at the centerline of the projection line of sight from the pinhole to the floor. The intensity varies as the square of the range. The exact method of adjusting this parameter may vary. However, by using line width, the same production process as the spot pattern may be used.

Measuring the angle of the line in the image allows use of a simplified position sensor on the position motor assembly, such as a gear tooth counter, to determine the rotational rate for real time operation of the motor and the angular information, in order to obtain the position of the camera bar from the floor line.

The structured light projector or projectors and camera may operate in a synchronized zoom mode, maintaining constant spot pattern spacing on the subject. The camera and structured light may be calibrated prior to shipment, i.e., at the factory.

The other patterns may be pre-distorted to give the proper pattern on the floor 1901 or wall. For example, the foot pattern may be projected approximately six feet in front of the supporting post of the camera bar. This is approximately 26.5° 1905 below the projector. (See FIG. 19).

The required lighting may vary depending on the particular range, size, and wavelength. For the NIR, the projection of the spots used in the structured pattern is one case.

The datasheet from Aptina (2008) gives the responsivity of the MT9V034 as $$\mathcal{R}_\lambda = 4.8 \frac{V}{lux \text{sec}} \quad (29)$$

where $\mathcal{R}_\lambda$ is the responsivity at the wavelength $\lambda=550$ nm.

From Cypress (2011), sensitivity is "a measure of pixel performance that characterizes the rise of the photodiode or sense node signal in Volts upon illumination with light." Units are typically V/(W/m²)/sec and are dependent on the incident light wavelength. Sensitivity measurements are often taken with 550 nm incident light. At this wavelength, 1/683 lux is equal to 1 W/m²; the units of sensitivity are quoted in V/lux/sec. Note that responsivity and sensitivity are used interchangeably in image sensor characterization literature so it is best to "check the units."

Photon Focus (2004) shows the equivalency of lux-sec to $$\frac{Ws}{m^2} \text{ to } \frac{J}{m^2}$$

at 550 nm from $$1 \text{Lux} = 1/683 = 1.464 \times 10^{-3} \frac{W}{m^2} \quad (30)$$

$$A_D = (6.0 \times 10^{-6})^2 \, m^2 = 3.6 \times 10^{-11} \, m^2 \quad (31)$$

By using the responsivity $\Re_\lambda$ given in Equation 29 and by dimensional analysis use the conversion factor for lux in Equation 30 and the area of the detector $A_D$ for the MT9V034 ($6 \times 10^{-6}$ on a side) in Equation 31 we may get a definition of lux per Watt for this specific detector.

$$\Re_\lambda = \frac{4.8[V]}{1.454 \times 10^{-8}\left[\frac{W}{m^2}\right] 3.6 \times 10^{-11}[m^2][s]} = 9.107 \times 10^{13} \frac{V}{J} \quad (32)$$

When the Aptina (2008) quantum efficiency (QE) is used, dividing the responsivity at one wavelength by the responsivity at a second wavelength gives $$\frac{\Re_{\lambda_1}}{\Re_{\lambda_2}} = \frac{QE_{\lambda_1}\lambda_1}{QE_{\lambda_2}\lambda_2} = \frac{0.464 \cdot 555}{0.34 \cdot 850} = 0.89107 \quad (33)$$

The value of this ratio may be used to give the responsivity at the second wavelength from $$\Re_{\lambda_2} = \frac{\Re_{\lambda_1}}{0.891} = 1.029 \times 10^{14} \frac{V}{J} \quad (34)$$

Aptina (2008) gives the voltage at saturation as 2.1V. From RCA (1974), to achieve saturation, the illumination on the focal plane for saturation has to be $$\Re_\lambda = \frac{v_\lambda}{E_\lambda} \rightarrow E_\lambda = \frac{v_\lambda}{\Re_\lambda} = \frac{2.1}{1.022 \times 10^{14}} = 2.055 \times 10^{-14} J \quad (35)$$

This is converted to an irradiance at the detector of $$\phi = \frac{E_\lambda}{A} = \frac{2.055 \times 10^{-14}[J]}{3.6 \times 10^{-11}[m^2]} = 5.7 \times 10^{-4} \frac{J}{m^2} \quad (36)$$

The integration time is dependent upon the frame rate. The maximum frame rate for a full height image using the selected sensor is 100 fps. The proposed design has 480 rows of pixels. Aptina (2008) limits the number of columns to 627, which reads:

The MT9V034 uses column parallel analog-digital converters, thus short row timing is not possible. The minimum total row time is 690 columns (horizontal width+ horizontal blanking). The minimum horizontal blanking is 61. When the window width is set below 627, horizontal blanking must be increased.

The frame time may be reduced by taking advantage of the short horizontal and long vertical requirement of the image and this will be considered in future builds of the system. The MT9V034 is capable of switching between two different contexts in real time. For example, it may have 628×314 for one frame and 630×480 for the next. For the present application context switch is not going to be used and the system will operate in Context A. In the form shown on Table 4 in the Aptina (2008) references gives the following equation:

$$F = V + (Nrows \times (A+Q)) = 4858 + (312 \times 690) = 220138 \quad (37)$$

$$T\_F = 220138 \times 37 \text{ ns} = 8.15 \text{ ms} \quad (38)$$

The times are the pixel counts times this value $$\text{FrameRate} = 122.65 \quad (39)$$

F is the total frame count. The frame rate is 1/F.
V is the vertical blanking, which is $$V = ((R0 \times 06) \times (A+Q)+4) = 7 \times (690+4) = 4858 \quad (40)$$

Minimum vertical blanking allowed is 7.
Q+A is the line width, which is a minimum of 690.
A is the window width (R0×04)=628

$$Q = P1 + P2 \quad (41)$$

is camera horizontal blanking. The minimum horizontal blanking is 61.

$$P1 = (R0 \times 05 - 23) = 39 \quad (42)$$

Line start blanking $$P2 = 23 \quad (43)$$

Line end blanking (Fixed Value)

$$Nrows = R0 \times 03 = 312 \quad (44)$$

The blanking will be adjusted to 14 lines achieve 120 fps.
Equation (39) gives the maximum frame rate is 122 Hz. A better rate analytically is 120 Hz. At 120 Hz frame rate, the detector flux is less than $$\varphi = \frac{5.7 \times 10^{-4} \frac{J}{m^2}}{0.00833} = 0.068 \frac{w}{m^2} \quad (45)$$

The design currently indicates that the Fujinon YV2.7× 2.2SA-2 megapixel vari-focal lens will be the best fit to the requirements. This lens has a wide angle of 2.2 mm and 2.7× zoom for a maximum focal length of 6 mm. The rationale for selection of this lens is discussed in the section titled "Zoom Lens". At the minimum focal length of 2.2 mm, this lens has an F/number ($F^\#$) of 1.3. This gives an effective aperture of $$F\# = \frac{fl}{D} \rightarrow D = \frac{fl}{F} = \frac{2.2\,\text{mm}}{1.3} = 1.7\,\text{mm} \quad (46)$$

The effective aperture varies slightly with focal length, but the calculated value is a good approximation for all focal lengths. At the maximum focal length, the effective aperture for the specified $F^\#$ is $$F\# = \frac{fl}{D_{CA}} = \frac{6}{1.7} = 3.5 \quad (47)$$

The literature gives the minimum walking distance for a subject using a regular stride on a path as long as 4.4 meters. If we are to set this as the required motion for the system, then, with the optical range as 3.6 meters, the operating focal length at that range is 4.2 mm. Thus, the $F^\#$ is $$F = \frac{fl}{D_{CA}} = \frac{4.2}{1.7} = 2.47 \quad (48)$$

RCA (1974) gives the required focal plane flux as $$\phi_{sc} = \frac{\phi_{fp} R T_r}{4(F)^2 (1+m)^2} \quad (49)$$

where $\phi_{sc}$ is the scene illuminance in $$\frac{J}{m^2}$$

$\phi_{fp}$ is the focal plan illuminance in $$\frac{J}{m^2}$$

R is the scene reflectance
$T_r$ is the lens transmission
m is the magnification from the scene to the detector faceplate.

In photographic systems which are neither macro nor micro, magnification is a very small number and may be neglected. At 2 meters, the height on the focal plane is related to the height in the scene as $$\frac{h}{fl} = \frac{H}{Z} \rightarrow m = \frac{h}{H} = \frac{fl}{Z} = \frac{0.0022}{2} = 0.0011 \quad (50)$$

To obtain a constant image size of the subject under test, this magnification will be constant over the range of operation. For the case of such a small magnification, $(m+1)^2 = 1.0022 \approx 1$ and thus may be neglected in the equation.

The original RCA equation is for equating lux on the scene to lux on the faceplate. Since lux-sec, at a given wavelength, may be readily expressed in terms of a constant multiple of $$\frac{J}{m^2},$$

we may express the equation in those terms because the constant on both sides of the equation would cancel. By rearranging for scene flux gives the flux for minimum range $$W_{sc} = \frac{4 W_{fp} F^{\#2}}{R T_r} = \frac{4 \cdot 0.068 \cdot 2.47^2}{0.70 \cdot 0.95} = 2.50 \frac{W}{m^2} \quad (51)$$

at 120 Hz frame rate.

At 3.6 meters, the required illumination power is $$E_{ill} = \frac{W_{sc}}{d^2} = 2.50 \left[\frac{W}{m^2}\right] \times 3.6^2 [m^2] = 32.4\,W \quad (52)$$

The system is calibrated against an eight foot by eight foot pattern of ¼ inch holes on one-inch centers. Specifically, it is fabricated from white pegboard with a surface of blacked flocked paper behind each hole. In addition, the pattern is repeated 26 inches across the floor.

The camera is suitably placed at the nominal 6 feet minimum range and the camera set to minimum focal length. The scene is imaged and the error from the black spots to the expected location is calculated. Thus, the camera is calibrated with the black spots. The distance to the pattern and the locations of the black spots are known.

Then, the pattern projector is turned on. If working properly, the pattern projector may place its light spot centered upon the black hole. Any asymmetry to the visible marks surrounding the hole is from errors. The distance from the black hole to the spot location is measured. Thus, the projector is calibrated.

Then, the platform is moved back incrementally until the maximum range is met. This produces a calibration table having error corrections for each focal length and light pattern film position. The number of increments may be determined during development. The initial presumption is to have at least three over the short range operational mode of a 12 foot path. That increment may be maintained through the entire range of the zoom lens. The development test facility may be limited to 20 feet.

Figure 20:
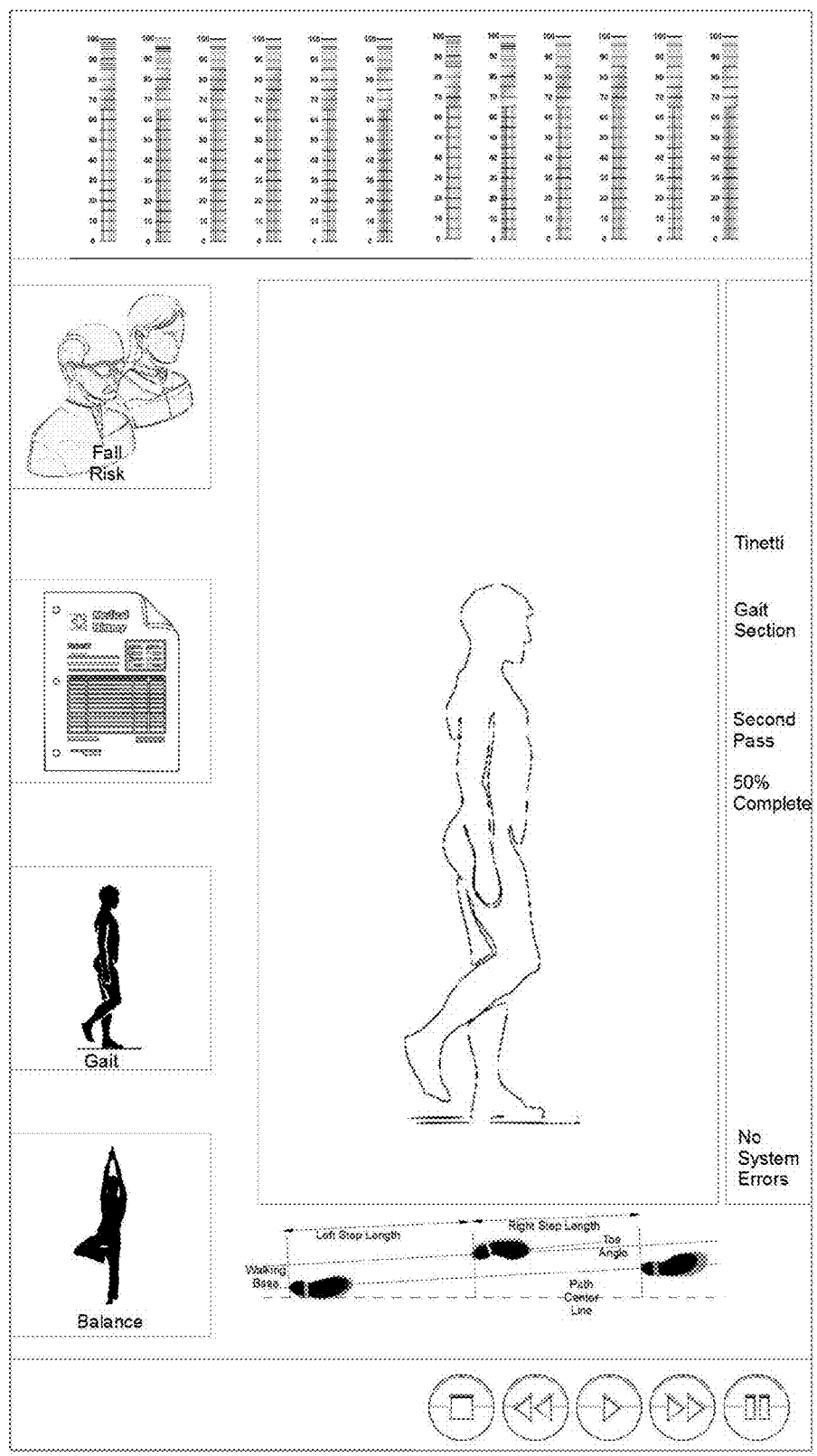
FIG. 20 is an illustration of a screen layout of an embodiment of a mobility monitoring system.

FIG. 20 illustrates one example of a conceptual screen layout.

The zoom lenses being used may be vari-focal lenses. The true zoom lens may be in focus throughout the range and the latter lens may not be in focus. Having to refocus is not a problem with this system because refocus may have to be done with a zoom lens. As the distance changes, the focal length is adjusted to maintain constant height of the subject. Hence, the focus is normally changed with the focal length when using a zoom lens in this implementation. The selected lens is a Fujinon YV2.7×2.2SA-2.

The focal length requirements for the baseline system are given in FIG. 24.

The rotational travel of the actuation for the zoom is approximately 62.5° in this embodiment. Focus travel is 84.5°. The drive for these two functions may have a ½ circle gear fastened in place by a screw holding an actuator lever. It is assumed that the pitch diameter is 58 mm. There are 60 teeth in the full diameter.

From inspection of FIG. 24, the maximum focal length change rate is at the maximum distance. Nominally, the rate of change is 1.4 mm/s for an individual walking 2 m/s. The focal length is nominally 2.2 to 5.4 mm or a range of 3.2 mm. Assuming the travel is linear, the maximum angular rate of 65.3°/s for the motor. This may be obtained by 10.9 revolutions per minute (RPM).

The maximum acceleration occurs when the subject passes in front of the system. This is nominally 2.1 mm/s$^2$. The maximum acceleration may be 0.92°/s$^2$.

The individual performance may depend upon the torque of and maximum RPMs of the motor along with the moments of inertial of the system. While this may be calculated with sufficient information, there is usually not sufficient information.

One suitable motor selection (54.5×20×13.8 mm) has 120 RPM maximum and 20 ounce-inches of torque. Gearing this down to 12 RPM may give 200 ounce-inches of torque.

A suitable NIR camera may be the Leopard Imaging LI-VM34LPCS. This camera has a CS mount lens, which is required by the Fujinon YV2.7×2.2SA-2. This camera may interface directly with the Pandaboard. This board may be used for development.

The camera board may include the camera chip, lens mount, two power converters, a number of passive components, and a connector.

One option for a baseline processor for the mobility monitoring system is a Texas Instruments OMAP4460 used on the Pandaboard ES. As these series of processors are upward compatible, the most recent version compatible with the developed software may be used. The OMAP4460 offers hardware implementation of image compression. The advantage of hardware implementation of image compression is that it contains real-time motion estimation and compensation. These serve useful in the tracking and joint segmentation.

The OMAP4460 high-performance multimedia application device is based on enhanced OMAP™ architecture and uses 45-nm technology.

The architecture is designed, but may be upgraded, to provide best-in-class video, image, and graphics processing for 2.5/3G wireless terminals, high-performance subjectal digital assistants (PDAs). For that purpose, the system supports the following functions: streaming video up to full high definition (HD) (1920×1080 p, 30 fps); 2-dimensional (2D)/3-dimensional (3D) mobile gaming; video conferencing; high-resolution still image (up to 16 Mp). The device may also support high-level operating systems ("Oss") such as: Windows™ CE, WinMobile™, Symbian OS™, Linux®, and Palm OS™. The device, in one embodiment, is composed of the following subsystems:—Cortex™, A9 microprocessor unit ("MPU") subsystem, including two ARM® Cortex-A9 cores, digital signal processor ("DSP") subsystem, image and video accelerator high-definition ("IVA-HD") subsystem, Cortex™-M3 MPU subsystem, including two ARM Cortex-M3 microprocessors, display subsystem, audio back-end ("ABE") subsystem, imaging subsystem "("ISS"), consisting of image signal processor ("ISP") and still image coprocessor ("SIMCOP") block, 2D/3D graphic accelerator ("SGX") subsystem, emulation ("EMU") subsystem.

The system, in one embodiment, includes state-of-art power-management techniques required for high-performance mobile products. Comprehensive power management is integrated into the device. The device also integrates on-chip memory, external memory interfaces, memory management, level 3 ("L3") and level 4 ("L4") interconnects, system and connecting peripherals.

In another embodiment, both processors offer part-on-part architecture for RAM. This configuration offers up to 2 GB of memory at a small fraction of an inch from the core.

The OMAP4430 offers the ability to strap two processors together for expanded pipeline operation. This embodiment may handle a throughput of up to 200 Mpixels/s.

The hardware specifications include super-scalar ARM Cortex™, A9.

1 GB LPDDR RAM, high-speed USB 2.0 OTG port optionally powers the board, on-board four-port high-speed USB 2.0 hub with 10/100 Ethernet, DVI-D (digital computer monitors and HDTVs), S-video (TV out), stereo audio out/in, high-capacity microSD slot and 4-GB microSD card, JTAG and one or more camera port.

The software specifications may include validation and demonstration image from the Angstrom Distribution. The Panda Board platform specifications include a first open OMAP™ 4 mobile software development platform with a OMAP4460 Processor. Highlights include a dual-core ARM® Cortex™-A9 MPCore™ with Symmetric Multiprocessing ("SMP") at 1 GHz each that allows for 150% performance increase over previous ARM Cortex-A8 cores, a full HD (1080p) multi-standard video encode/decode, imagination Technologies' POWERVR™ SGX540 graphics core supporting all major API's including OpenGL® ES v2.0, OpenGL ES v1.1, OpenVG v1.1 and EGL v1.3 and delivering 2× sustained performance compared to the previous SGX530 core, and low power audio.

Technical specifications, in one embodiment, may include core logic, a display, memory, audio, connectivity, wireless connectivity, expansion, debug and dimensions. The core logic includes a OMAP4460 applications processor. One embodiment of a display is a HDMI v1.3 Connector (Type A) to drive HD displays including DVI-D Connector (may drive a 2nd display, simultaneous display; which would need an HDMI to DVI-D adapter) and LCD expansion header. The memory may be a 1 GB low power DDR2 RAM with a full size SD/MMC card cage with support for High-Speed & High-Capacity SD cards. Audio includes a 3.5" audio in/out and HDMI Audio out. The connectivity may be an onboard 10/100 Ethernet. Wireless connectivity may be 802.11b/g/n (based on WiLink™ 6.0) and Bluetooth® v2.1+EDR (based on WiLink™ 6.0). Expansion may include 1×USB 2.0 High-Speed On-the-go port, 2×USB 2.0 High-Speed host ports, general purpose expansion header (I2C, GPMC, USB, MMC, DSS, ETM) and camera expansion header. The debug specifications may include JTAG, UART/RS-232, 2 status LEDs (configurable), and 1 GPIO Button. It is contemplated that the system dimensions may include a height of 4.5" (114.3 mm), a width of 4.0" (101.6 mm) and a weight of 2.6 oz (74 grams).

It is contemplated that the display SoC may perform a number of tasks including: process the imagery from the cameras' SoCs; associate anthropometric data from the database with the imagery and mesh model, derive biomechanical data from motion data, formatting biomechanical data to be compatible with OpenSim, provide a 0 to 100 score on current performance, compare current performance with nominal for the subject's age, weight and height, compare current performance with subject's historical data, render 3D color image, generate skeletal figure, render 'ghost' or shadow of past performance, nominal case and both, control the interface functions with the touch panel, maintain subject's records and transfer to practice's system, communicate to maintain records and update database or firmware, conduct built in test, power up test, etc., take system to 'sleep mode' and re-awaken, monitor power such as mains status and battery reserve (estimated time), generate footprint on display, and give instructions to the operator and subject such as verbal and projection of icons, and execute photoplethysmographic processing.

The functional pages to the control panel may include: enter subject data, identify test type, specific standard test, tinetti gait and balance, timed up and go, specific functional assessment, range of motion assessment, gait assessment, balance assessment, activities of daily living ("ADL") assessment and start test.

In one embodiment, only a few icons may be shown at any one time. For example, the greeting screen may give the operator the choice between "Returning Person" and "New Person." This function may be available on an internal network, allowing the practitioner the ability to prescribe the desired assessment directly to the instrument. If one of the intranet or internet deployed databases are used, the operator may also have the subject's record available at the time of testing or other time, as needed.

The Left Camera imagery data bus is connected directly to the Right Camera. The Right Camera multiplexes the imagery from the two cameras by alternating pixels.

The Stereo SoC may contain functions that include: exposure control, autofocus, illumination control, autozoom (fixed height between spots), de-multiplex stereo imagery, detect spots, detect line, range calculation, velocity calculation, subject mesh generation, joint location calculation, foot impact angle calculation, and calibration corrections.

The color camera suitably has a dedicated processor and may use the same zoom lens as the NIR cameras. The color camera's processor may fuse range information from the processed stereo data to arrive at a rendered three dimensional image. The color image may be used to subtract background and provide a template of valid subject regions to the stereo processor, thus limiting ambiguity.

The Color SoC may contain functions including: exposure control, autofocus, autozoom, centroid tracking, calibration corrections, silhouette segmentation, background subtraction, calculation of footprints, range gating, and tracking head control system.

The stand may preset the height of operation and position of the camera and control panel. The other units may be removable for ease of storage and snap securely into place when ready for use. The stand suitably has a docking station and the weights in the base are suitably batteries to ensure full day operating time without use of power from mains or other power outlet. Since batteries are suitably used, one advantage of the system is that there are no cables on the floor for someone to trip over or accidentally unplug the system. The docking station may be flush against the wall (or baseboard) and the base may be keyed to align it upon docking. The vertical support member of the stand may be sectioned or a single shaft. The shape may be any cross section.

The stand may contain the projector for the NIR line on the floor to give 'on the fly' position calibration to the NIR cameras. The projector may project the starting position for the subject, the direction of travel, turnaround time, etc. for gait assessment. For ADL, drawers and doors may be projected for the subject to "open" to gauge minimum flexibility. Other functions may be added. The projectors may contain one 'slide' each or a 'slide' changing mechanization.

An expanded mobile monitoring system embodiment suitably adds a foot camera 504 at the foot and overhead camera 501 as shown in FIG. 5. The Overhead Camera 501 is able to image the dots. The dots are a function of the distance from the camera and the height above ground. By fusing the data from the cameras with stereo imagery, a more robust map of the point cloud is obtained. There may be an advantage in additional data to use in calculations by adding these two cameras.

Figure 23:
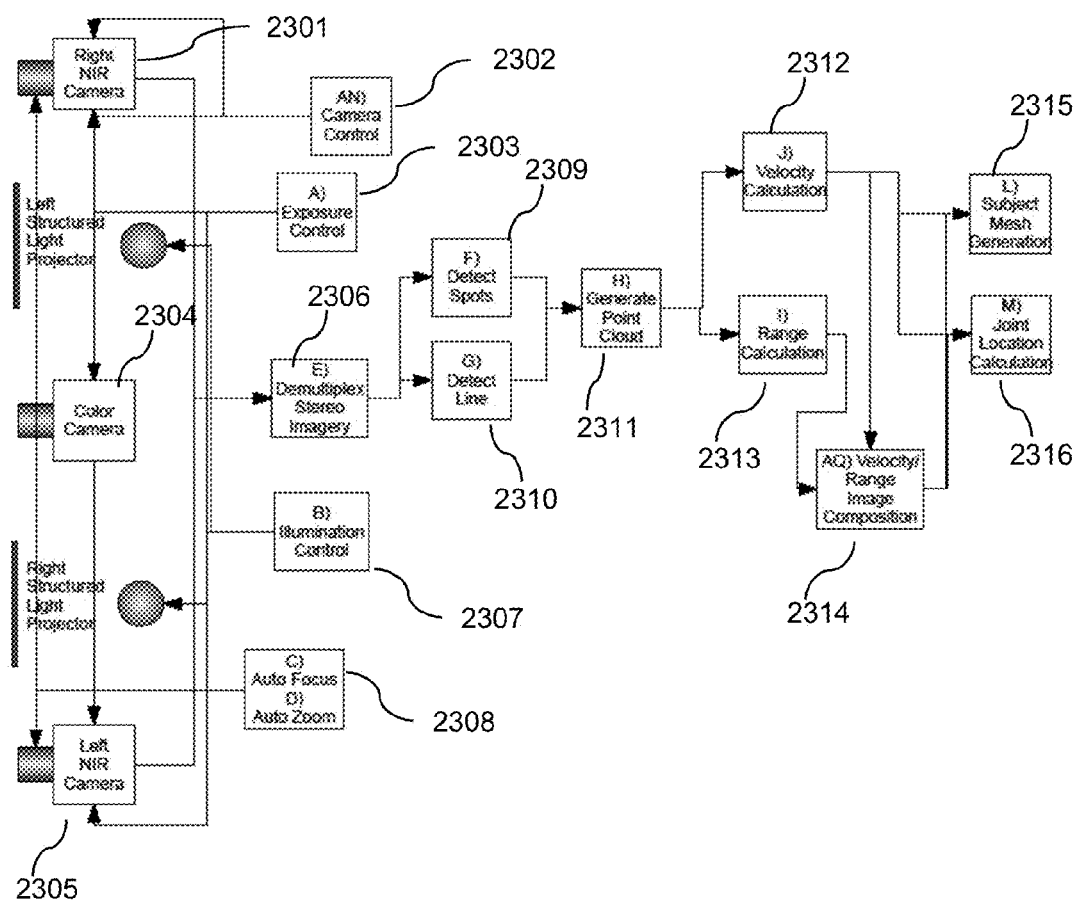
FIG. 23 is a mesh generation function block diagram of a mobility monitoring system.

The Foot Camera 504 is able to see the strike time of the heel. The heel strike may be the point of reference for stride length. In addition, the angle of the foot camera may give a more accurate representation of the foot angle throughout the stride. FIG. 23 shows an embodiment of an expanded mobility monitoring system block diagram.

The Foot SoC contains functions including: exposure control, autofocus, autozoom, detect spots, detect line, generation of the subject convex hull, range calculation, velocity calculation, subject mesh generation, joint location calculation, and calibration corrections. The Foot SoC also contains functions including: foot impact angle calculation and heel strike time detection.

For Structured Light, the exposure control in this particular design places a priority on increasing the illumination such that a constant level of light falls on the focal plane. This may be extended by increasing the exposure time when the range or view angle is sufficient to limit the motion during an exposure. The control of the illuminator is within the Stereo SoC. Exposure control may be a combination of light level via the illumination control and exposure time via the camera chip. The foot camera and overhead camera, if used, receive the shutter data from the Stereo SoC.

For the color camera, the light level may be set by the environment. Exposure control may be the shutter speed (and iris if need). This function resides in the Color Camera SoC.

Illumination control is another processing function. The light level may be reduced by a number of factors. In this particular embodiment, the light level on the transparency is reduced with the square of the distance from the pinhole. The projected light is reduced with the square of the distance from the light source to the subject. The reflected light from the subject is reduced as the square of the distance between the subject and the camera. The light on the focal plane is decreased with an increase in F-stop. The F-stop increases with focal length. The focal length increases in proportion to the distance, in order to maintain constant scale on the focal plane. The light source may be appropriately sized to achieve proper illumination at the maximum design range.

This function may be closed loop with the camera. That is, an error signal is generated by the camera when the light is not correct and it is passed to this function, which minimizes the error by increasing or decreasing the illumination.

Autofocus and autozoom are additional processing functions. There are a number of known algorithms for autofocus control. There are options available from known SoC vendors. However, it is possible that a particular algorithm may be modified as needed. Autozoom is a fixed height between spots. The structured light pattern selected may provide a spot centroid every 5 pixels over the target. The size of the projection of the structured light pattern is controlled by the range to a subject's centroid. The auto-zoom function may maintain this spacing over the operational range between the system and the subject. The current design concept uses the region of interest around the center pixel for verification of the correct size for the zoom control system. Zooming may be fine-tuned by the size of the spot pattern at the center.

Upon the subject being placed at the correct location, the processing measures the spacing. Spot centroid locations may be located to within a fraction of a pixel related to the diameter of the spot. A well-known rule of thumb in machine vision is that a spot which is nominally a single pixel in diameter may be located to within $1/5$ of a pixel and the location precision is inversely proportional to the number of pixels in the spot (or width of line). If a spot has four pixels, then the centroid may be located to within 1/20 of a pixel.

As stated above, the camera architecture allows for the processing function of multiplexing of the stereo imagery. In the particular architecture depicted in FIG. 23, the right camera is the master and thus the first pixel is right and the second is left. This pattern is repeated throughout each line. Thus, the processor suitably assigns each right pixel to the right image starting with the first pixel of each line and assigns each left pixel to the left image starting with the second pixel of each line.

Detect spots is yet another processing function. Sundry filtering techniques may be used to emphasize the spots over the background imagery. With the four different spot diameters, it is conceivable that there may be four filters to discriminate between spot labels.

Measurement of the spot center includes the filter to detect the spot suitably does not affect the measurement of the centroid. Rather, an ideal filter may present the spot location to a fraction of a pixel.

Detection and location of the spots is similar to detection of spots in gel arrays and processes. The detection and location of the spots are fundamentally similar in that they are on or near centers, have stray artifacts, there are variations in size (by light source design), and there is spot overlap (as a curved edge is approached).

Detect line is another processing function. The infrared line projected upon the floor should be detected to assist in the calculation of some parameters of motion. In particular, this includes the foot angle. The centerline may be detected to a fraction of a pixel. Thus, the angle between the foot and the floor may be detected to within a fraction of a pixel.

Line detection may be performed by a mid-level image processing algorithm. After the line is enhanced by using the one dimensional equivalent of the spot detection filters, it is "thresholded" and the edge is "presented" to a Hough transform which maps it to a best fitting edge.

Other lines may be useful in an expanded system. For example, a line pattern may represent a cupboard from which the subject is instructed to insert and remove objects (or simulated objects). This may be detected in the color image and used to assess the subject's performance for that task.

With a range calculation processing function, two aspects of range are suitably calculated. One is the range from the camera to the intersection of the spot with the subject. This is the absolute range between the system and the subject. It is suitably accurately detected. This range may be determined photostereogrammatically from the line or spots using standard stereo correspondence algorithms. The spot detection and line detection provide unambiguous locations for correspondence.

The overall range to the subject is the suitable resource available to constrain the above calculation. The range may be determined from the geometry of the optical centerline of the camera bar and the "fixed" line projected on to the floor. The distance from the camera base to the line is known along with the height of the camera bar above the floor. The image angle is detected as part of the line detection process, which is transformed into the angle of the line with respect to the camera. This angle between the camera and the line is desired for measurement of the range to the centroid.

Once the angle is known, simple trigonometry may be used to derive the range to the subject. Other factors may be used to enhance this measurement, for example, the focus and zoom may be calibrated to range. Reading the focus position would give the range to the subject. The zoom position may be used to calculate the angle. By determination of the height at the initial range, the distance that would give that same screen height at the given focal length may be used to determine the range. These measures may be fused to enhance the accuracy and repeatability of the range calculation.

The processing function of velocity calculation includes the motion of each spot in pixels (and fraction of pixels) per frame. When this motion is converted to angular rate and combined with the range to the subject, the local velocity in meters per second may be determined.

This calculation may be further enhanced during the processing of the point cloud generated using the spot pattern from the structured light. This processing gives the three-axis velocity of each spot.

Subject mesh generation is the three dimensional point of impact with the subject of the projection of each spot from the structured light may be determined from stereophotogrammatic equations. There are multiple methods capable of determining the location with the present architecture. These methods include angle displacement between cameras; angle displacement between left camera and light source; and angle displacement between right camera and light source.

These methods may be fused to arrive at a more accurate measurement of location. Likewise, a tensor analysis for trinocular vision may be exploited. The current implementation chooses to fuse the three measures with the generation of the convex hull K.

The three dimensional loci of the spots from each frame represent the point cloud from the given viewing angle. The point cloud from each successive frame may be fused to obtain a point cloud representing the full body of the subject.

Once a satisfactory point cloud is attained, it may be faceted and normals to the surface at each facet may be calculated. The fact that each horizontal cross section is quite accurately modeled by an ellipse and the smooth movement of the vertical surfaces may be exploited to minimize the impact of loose clothing. The "corrected" faceted model then becomes the mesh model of the subject.

The local frame to frame motion of each spot may then be used to "animate" the mesh model of the subject to obtain the three-axis motion of the body from frame to frame.

With generation of the subject convex hull, the convex hull is the 'contour map' along the axis of interest. A convex hull of a subject's face may be obtained by tracing the centerline of the stripes from a Ronchi ruling. Spots are expected to provide the same convex hull.

This is particularly useful in generation of a 3D map of the subject at the initial position. Many motion analysis systems have the subject turn with arms out for calibration. One turn each with arms down, arms out and arms up would give a very accurate point cloud model of the subject for initial conditions. Motion of each joint would allow identification of their locations before walking (or other activities) started. The turn-around function may be achieved by the half-turn at the end of each walk.

This initial model may serve as the three dimensional space map upon which to project the new data for assessment of data quality and refinement of the mesh model.

Joint location calculation includes the motion of the ensemble of points to be used to back project the center of rotation. This may be used in conjunction with a skeletal model of the subject derived, first from their variation from the norms as found in an anthropometric database and from similar models of the human muscular-skeletal system such as available in OpenSim and various sites such as Defense Technical Information Center Online.

Figure 21:
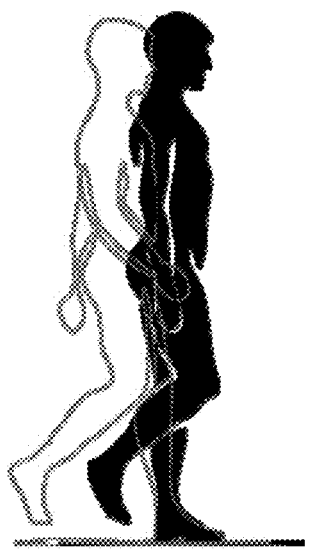
FIG. 21 is an illustration of foot fixed motion of a subject.
Figure 22:
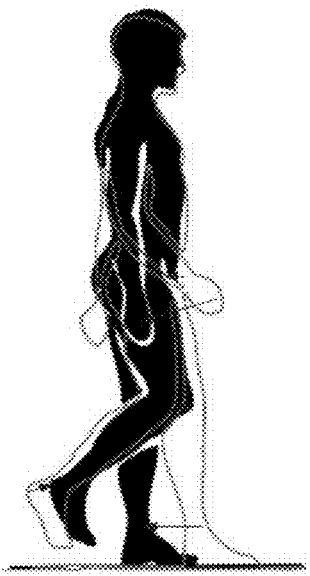
FIG. 22 illustrates body fixed motion of a subject.

The sample image of FIG. 21 shows the motion from one frame (violet line to black silhouette) The image of FIG. 22 shows the body fixed and the relative foot motion with respect to the body.

The foot angle calculation may be approximated using the stereo cameras. With the information from this calculation, the floor level camera in the expanded system provides a more accurate measure. When the view angle for the cameras are suboptimal, the model derived may be used to derive the angle thus sense variations of the angle during walking. This information may be used to enhance the lower regime of the mesh model.

The foot level camera may be equipped to track problems such as foot droop or improper impact angle. Heel strike time detection is where the human stride is analyzed from heel strike to heel strike. Measuring this strike time with great accuracy directly reflects in the measurement of the stride length and time, two walking parameters which may be used in mobility assessment. With most cameras, the frame rate may be increased by using fewer lines and fewer pixels per line. For the moment, if overhead clock cycles are ignored, then a camera which gives 100 frames a second would give 200 frames per second (fps) at ½ frame, and 400 fps at ¼ frame.

In the normal range of walking, the foot is seldom more than a few inches off of the floor. The normal toe clearance may be nominally ¼ inch (0.55 cm). The ankle may ride somewhat higher, but six or seven inches would get most people to mid ankle. Thus, we may use the same camera to image the foot at much higher rates than the whole body. At 400, the sample time is 2.5 ms. The heel strike transient is often approximately 35 ms in length.

A higher frame rate is needed in the analysis of foot movement. Thus, only having the high speed camera in place for foot movement minimizes cost in both computational and financial terms. But alternate embodiments may include more high speed cameras, especially if financial restraints are not a factor.

Calculation of footprints is gathered from data acquired with the stereo cameras, the position of the feet with respect to the path may be determined. The overhead camera and the foot camera may enhance the performance of this metric.

By using the cameras, a path of the footprints showing the way the subjects walks is generated. This image may clearly depict the walking base and stride length. Behind the footprints, a color coded depiction of the subject's historical tests or norms for their age, height and weight may be displayed. In this particular case, significantly below normal would be red and normal or better would be displayed green. Normal may be with respect to the subject's past performance. The range in between would be displayed yellow. However, other color combinations are possible.

In the context herein, centroid tracking refers to maintaining body centroid in the color frame. The color camera maintains a trunk of the body in the center of the screen. The camera may use motion estimation from motion compression to generate the error signal to the camera bar position control system. The centroid tracker may use the data from the mesh model to mask extremity motion and aid in silhouette segmentation.

Silhouette segmentation is where the color camera may be used to attain a silhouette of the subject. This may serve in multiple roles. When segmented, it may allow generation of a region of interest, the outside of which the spot detection scheme may ignore. Background subtraction aids in the generation of the silhouette. Motion of the centroids of the extremities allows for synthesizing the joint locations in the mesh model.

By imaging the room before the subject is put in place, the system may generate a rough template for the subject known as background subtraction. As it tracks the subject, the surrounding area is the background. This surrounding area in turn may then be used to discard background for the next layer of processing.

Range gating may set the maximum range at which data is valid to limit unnecessary processing. The function of a range gate is to set the region of interest for measurement. For example, if the calculated range for a particular spot was much less or much more than its nearest neighbor spots, then the spot may be discarded and an estimation made from the nearest neighbor spot.

Additionally, the region of interest may limit the number of needed calculations. The range data combined with the data derived from the silhouette may reduce the calculations by a factor of four or more.

One of the main discriminators between the system described herein and other motion analysis systems is maintaining constant viewpoint and scale of the subject's motion. The maximum rate is seen with the foot at 6 m/s. At 100 fps, this is 6 cm per frame. At 400 fps, this reduces to 1.25 cm per frame. The tracking head control system receives position information from the Tracking Drive and error information from the Centroid Tracking.

In processing the imagery from the cameras, the three cameras on the camera bar and the upper (overhead) and lower (foot) cameras present preprocessed information to the control panel. However, there may be further processing before this data is ready for archiving. This function performs post processing on the source imagery.

With associate anthropometric data from the database with the imagery, the system has created a mesh model of the subject and identified the likely joint locations from the tracking of the limbs. Anthropometric metric data provides maximum likelihood locations for the joint and may score the results of the preprocessing to make it match the measurement. The processing identifies the 'true' joint locations by using the anthropometric metric data to establish the most likely location of the joint, thus constraining the estimation. However, the 'true' joint location from the subject is compared to the anthropometric data to identify variations from the norm in joint structure.

Biomechanical data may be derived from motion data. This function generates angular rates and acceleration of the limb's sections. This information may be passed to generate it in a traditional biomechanical format.

In formatting biomechanical data to be compatible with OpenSim, the data transmission standards from clinical motion analysis may prove useful in exchanging the information within the medical community.

By putting such standards into biomechanical terms, the standards serve as a more refined way of communicating the issues to a full motion analysis laboratory, if needed.

The system may provide a 0 to 100 score on current performance that is presented on color-coded gauges. In the United States, the traditional scoring system in schools is 0% to 100%.

Therefore, most people intuitively understand a scale of that type. The data acquired by the system may be converted to this scale for ease in understanding performance, however other scales are contemplated.

In this embodiment, the sub-elements are scored with integer values. By giving those elements continuous scores determined from the norms for the subjects age, weight and height, the score becomes continuous. If the score is renormalized to 100, then it may meet suggested criteria (some scores may not be linear). ROM readily lends itself to 0 to 100 by re-normalizing to maximum human limits. ADL/IADL includes a number of scoring systems that may be renormalized to 0 to 100.

Current performance may be compared with nominal for the age. There is a lot of data available to characterize age norms. This data not only may be used to show the subject where they stand relative to a norm, but the curves of the norm may be used to predict where the subject may be in one to five years if no intervention action takes place. Or, the norm curves may be used to predict when the subject may require placement in assisted living.

Current performance may also be compared with a subject's historical data. Comparing with past performance allows a subject to identify their progress or regress during the interim. Of particular interest would be to use it and the norm data to personalize the prediction. If the subject is undergoing a corrective regimen and is seeing progress, this data may serve as a motivator to continue.

A 3D color image is rendered by transmitting the range information interleaved with the pixel color information. Therefore, the 3D range information now available may be combined with the color information to render a 3D image if a supporting screen is available.

A 'ghost' may be rendered indicating past performance, nominal case and both. This tool is helpful concerning the motivational aspects of the system. A 'ghost' silhouette is placed behind the subject which is animated by the norms for the subject or the historical data from the subject. It may be color coded as the footprints.

Interface functions may be controlled by the touch panel. This serves to read the touch inputs and convert them to commands. It may be multitouch enabled to allow manipulation of the imagery such as zooming or changing the viewpoint.

A subject's records may be maintained and transferred. This is a file handling system which serves as part of the archive function. It also may be set up to communicate with other machines including those storing physicians (or other practitioner's) record keeping systems.

The system communicates to maintain records and update the database or firmware. This function allows communication over a network or wirelessly to a central system to allow updates and transfer records. Examples include Wi-Fi, Ethernet, Internet, Zigbee, USB or some other system.

The system may conduct a built-in test, power-up test, etc. For the most part, graceful degradation may not be notable with this system except for the drive motors. Therefore, the built in test may only be able to note hard failures. However, with some functions redundant, the test may be designed such that some failures may not result in disabling the system. For example, the loss of one stereo camera should have little effect on overall performance when using it for mobility assessment.

The system may also include a 'sleep mode' and re-awaken. One design has the system docked before use and docked after use. By placing batteries in the base of the stand, this would allow operation for a full business day off of mains. Thus, it may suitably eliminate the need for a dedicated room or area to perform the analysis.

Power may be monitored, for example, if operating off of mains or for the case of power loss, the remaining capacity of the batteries is important. This function gives an estimate of the amount of time remaining on battery operation.

A footprint "path" may be generated on the display. This function is the manifestation of the display of the calculated footprint positions.

The system further provides instructions to the operator and the subject. The development process may have a script for the operator and another for the subject. The execution of this script results in either verbal commands or icons projected on the scene (for the subject) or the screen (for the operator).

The system also executes photoplethysmographic processing. The difference between two (or more) wavelengths on a point of skin may be used to generate photoplethysmographic data. This data may be used to report blood pressure, dissolved oxygen, pulse rate and heart beat artifacts of the subject. This data may also be used with color imagery.

The bare flesh of a subject may be detected by the color camera when using red versus green. The color camera combined with the overhead camera may be used to obtain the factors from photoplethysmography. This fused measure provides important parameters of the subject's response to the exercise in the mobility analysis.

If the overhead camera (or foot camera) is used, a suitable embodiment would include illuminating at least two NIR wavelengths during successive frames at times other than the coincident usage by the stereo camera. Because the convex hull does not need to be updated at the same rate as the stereo cameras, the frame rate may be such that every third frame is coincident. Because the stereo cameras (in the baseline design) are operating at the maximum frame rate, the overhead camera may suitably have to be at ⅔ the frame rate of the stereo camera. Other configurations may have the overhead frame rate at 3 times the stereo camera.

In the baseline system, the spot camera is at 0.85 μm. This may be the full field illumination for one of the two photoplethysmographic frames. The other may be typically at a shorter wavelength to enhance performance, if a silicon imager is used. An additional wavelength may be added just above the red wavelength. The overhead camera may be dedicated to every other frame at the shorter wavelength.

A further enhancement involves an additional camera specifically designed for photoplethysmographic imaging. The design may use two spot projection sources at wavelengths optimized for detection of blood oxygen and blood flow.

During assembly of the system, the cameras may be calibrated against a test pattern which replicates the generated spots. The generated spots may then be used to calibrate the projection system against the cameras. The data derived from these processes is stored and used for calibration when the system is used in the field.

The cameras may need a number of commands for setup of a particular configuration. The controller handles these functions. This includes exposure time, start and stop pixel and start and stop line.

This function takes the current frame velocity calculation and range calculation and generates a composite image containing the local estimation of the range and velocity of every pixel by interpolation between the spot centroids.

The functional interconnections requirements for generation of the subject mesh are shown in FIG. 23. This diagram also shows the interrelationship between several of the functions.

In summary, the apparatus, system and methods provided and described herein include a three-dimensional imaging apparatus for analyzing motion of a subject. The apparatus suitably includes one or more structured infrared light projectors for projecting near-infrared structured light onto a subject; a plurality of near-infrared cameras for capturing motion of the subject by detecting reflected structured light; the cameras and the one or more structured infrared light projectors operatively coupled to the subject; and a processor, operatively coupled to the structured light projector and the cameras. The processor is programmed to convert the reflected structured light into motion data of the subject. The structured light projector has an integrating sphere having a pinhole; two or more infrared light emitting diodes projecting inside the integrating sphere; the light emitting diodes operating in a simultaneously flashing pulsed mode in synchronization with exposure times of the plurality of cameras; and a film pattern located between the pinhole and the subject to produce a structured light pattern projected onto the subject. The apparatus may also include a display device coupled to the processor, in which the display device is capable of showing motion data. The apparatus may also include a camera bar, wherein the plurality of cameras and the structured light projector are mounted on the camera bar. The apparatus may also include a color camera.

The structured light projector projects illuminated spots on the subject; the spots are aligned in a two-dimensional plane and the centroids of the spots are equally spaced along both axes of the two-dimensional plane. The apparatus autonomously rotates to hold the subject's trunk at the center of a field of view.

The processor is further configured to compare the motion data of the subject to saved data to determine a level of mobility of the subject, and may include separate, rotatable projectors. The processor yields a conclusion as to proposed means for rehabilitating or strengthening the subject to compensate for the observed error. The comparison yields a conclusion as to whether the subject may function independently or requires assistance. The apparatus creates an individual mesh model which is used to create a shadowing avatar; the avatar includes either the subject's prior performance or a ghost figure representing the normal range for the subject's age. The infrared cameras are rotated 90 degrees so they function in a portrait-style mode. The patterned film contains spots, the spots being individually identifiable by two near-infrared cameras; the cameras identification creating a three-dimensional point cloud. The film size may be suitably increased up to 54 mm. The apparatus adjusts the distance from the pin hole to the film to give an angle such that it projects a grid of spots at the subject's centroid.

Also provided is a method for analyzing a subject's motion, which includes projecting structured light onto a subject to generate structured light images of the subject's motion; recording a plurality of structured light images via a plurality of near-infrared cameras as data sets; processing the data sets to generate 3D images of the subject's motion; and comparing the 3D images to stored data to detect deficiencies in the subject's motion. The method may also include generating rehabilitative exercises targeted to compensate for observed deficiencies in the subject's motion, and also include the step of relaying the results to a physician for diagnosis. The method may also include tracking the motion of the subject automatically, the tracking comprising maintaining the trunk of the subject at the center of a field of view; processing the data from the plurality of cameras and the structured light projector to produce a three-dimensional point cloud; and mapping the three dimensional point cloud onto a mesh outline of the subject.

Also provided is a system for generating three-dimensional images of motion of a subject, which includes a stand component having a base member and a support member extending from the base member; a camera bar connected to the support member and distally opposed from the base member. The plurality of near-infrared cameras are mounted on the camera bar; a structured near-infrared light projector mounted on the camera bar, the structured near-infrared light projector operatively coupled to the subject and producing structured light onto a subject and coupled to the motion of the subject; a processor programmed to communicate with the plurality of cameras and the structured light projector and programmed to convert the structured light into motion data of the subject; the processor further configured to compare the motion data of the subject to stored data to determine a level of mobility of the subject.

The foregoing description is considered as illustrative only of the principles of the embodiments described herein. Further, since numerous modifications and changes may readily occur to those skilled in the art, it is not desired to limit the embodiments to the exact construction and operation shown and described, and accordingly, all suitable modifications and equivalents are considered to fall within the scope of the embodiments. Various features and advantages of the embodiments and processes described herein are set forth in the following claims.

All publications, patents and patent applications referenced in this specification are indicative of the level of ordinary skill in the art to which this application pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

The following references are incorporated in their entities by reference herein.

REFERENCES

Aptina (2008) ⅓-inch Wide-VGA CMOS Digital Image Sensor MT9V034 [Data Sheet]

GS Settles (2001) Schlieren and Shadowgraph Techniques: Visualizing Phenomena in Transparent Media, Springer, Berlin Cypress (2011) STAR1000 1M Pixel Radiation Hard CMOS Image Sensor, [Data Sheet] Cypress Semiconductor Corp, San Jose, Calif.

Photon Focus (2004) Photometry versus Radiometry, AN008 V1.1, Photonfocus AG Locken Switzerland RCA (1974) Electro-Optics Handbook, EOH-11 Lancaster, Pa.

What is claimed is:

1. A three-dimensional imaging apparatus for analyzing motion of a subject, comprising:
   one or more structured infrared light projectors for projecting near-infrared structured light onto a subject;
   a plurality of near-infrared cameras for detecting reflected structured light and capturing motion of the subject, the cameras and the one or more structured infrared light projectors physically coupled to the subject; and
   a processor, operatively coupled to the structured light projector and the cameras, the processor programmed to convert the reflected structured light into 3D motion data of the subject.

2. The apparatus of claim 1, wherein each of the structured light projector includes:
   an integrating sphere having a pinhole;
   two or more infrared light emitting diodes projecting inside the integrating sphere, the light emitting diodes operating in a simultaneously flashing pulsed mode in synchronization with exposure times of the plurality of cameras; and a film pattern located between the pinhole and the subject to produce the structured light as a structured light pattern projected onto the subject.

3. The apparatus of claim 2, wherein the film size is increased up to 54 mm.

4. The apparatus of claim 2, wherein the processor is further configured to adjust the distance from the pin hole to the film to give an angle such that it projects a grid of spots at the subject's centroid.

5. The apparatus of claim 1, further comprising a display device, coupled to the processor, for visually presenting the motion data.

6. The apparatus of claim 1, further comprising a camera bar, wherein the plurality of cameras and the structured light projector are mounted on the camera bar.

7. The apparatus of claim 1, further comprising a color camera operatively coupled to the plurality of near infrared cameras and the subject.

8. The apparatus of claim 1, wherein:
the structured light pattern produces illuminated spots onto the subject; the spots being aligned in a two-dimensional plane with the centroids of the spots being equally spaced along both axes of the two-dimensional plane.

9. The apparatus of claim 8, wherein the spots are individually identifiable by two near-infrared cameras, to generate a three-dimensional point cloud, and map the point cloud onto a mesh model.

10. The apparatus of claim 1, wherein the processor is further configured to compare the motion data of the subject to stored prior motion data of the subject and representative normal motion data to determine a level of mobility of the subject, and is further programmed to include stored data of rehabilitation and strengthening exercises.

11. The apparatus of claim 10, wherein the processor is programmed to generate a conclusion proposing rehabilitating or strengthening the subject from the stored data of rehabilitation and strengthening exercises to compensate for an observed deficiency between the motion data of the subject and the stored prior motion data of the subject and the representative normal motion data.

12. The apparatus of claim 10, wherein the processor is programmed to generate a conclusion as to whether the subject may function independently or requires assistance.

13. The apparatus of claim 1, wherein the processor is further programmed to create a shadowing avatar from an individual mesh model, the avatar comprising either the subject's prior performance or a ghost figure representing the normal range for the subject's age.

14. The apparatus of claim 1, wherein the infrared cameras are rotated 90 degrees to function in a portrait-style mode.

15. A method for analyzing a subject's motion, comprising:
physically coupling a plurality of near-infrared cameras to the subject;
projecting structured light onto a subject to generate structured light images of the subject's motion;
recording a plurality of structured light images via the plurality of near-infrared cameras as data sets;
processing the data sets to generate 3D images of the subject's motion; and
comparing the 3D images to stored prior motion data of the subject and representative normal motion data to detect deficiencies in the subject's motion.

16. The method of claim 15, further comprising generating rehabilitative exercises targeted to compensate for observed deficiencies in the subject's motion.

17. The method of claim 15, further comprising transmitting the results to a physician for diagnosis.

18. The method as in claim 15, further comprising:
tracking the motion of the subject automatically, the tracking comprising maintaining the trunk of the subject at the center of a field of view;
processing the data from the plurality of cameras and the structured light projector to produce a three-dimensional point cloud; and
mapping the three dimensional point cloud onto a mesh outline of the subject.

19. A system for generating three-dimensional images of motion of a subject, comprising:
a stand component having a base member and a support member extending from the base member;
a camera bar connected to the support member and distally opposed from the base member;
a plurality of near-infrared cameras mounted on the camera bar;
a structured near-infrared light projector mounted on the camera bar, the structured near-infrared light projector physically coupled to the subject and producing structured light onto a subject and coupled to the motion of the subject;
a processor programmed to communicate with the plurality of cameras and the structured light projector and programmed to convert the structured light into 3D motion data of the subject; the processor further configured to compare the motion data of the subject to stored prior motion data of the subject and representative normal motion data to determine a level of mobility of the subject.

* * * * *